(12) United States Patent
Foster et al.

(10) Patent No.: US 11,759,438 B2
(45) Date of Patent: Sep. 19, 2023

(54) COMPOSITIONS AND METHODS FOR TREATING OCULAR PATHOLOGIES

(71) Applicant: The Board Of Supervisors Of Louisiana State University And Agricultural And Mechanical College, Baton Rouge, LA (US)

(72) Inventors: Timothy Paul Foster, Slidell, LA (US); Charles David Nichols, New Orleans, LA (US)

(73) Assignee: The Board of Supervisors of Louisiana State, Baton Rouge, LA (US)

( * ) Notice: Subject to any disclaimer, the term of this patent is extended or adjusted under 35 U.S.C. 154(b) by 173 days.

(21) Appl. No.: 16/610,382

(22) PCT Filed: May 1, 2018

(86) PCT No.: PCT/US2018/030448
§ 371 (c)(1),
(2) Date: Nov. 1, 2019

(87) PCT Pub. No.: WO2018/204359
PCT Pub. Date: Nov. 8, 2018

(65) Prior Publication Data
US 2020/0330405 A1    Oct. 22, 2020

Related U.S. Application Data

(60) Provisional application No. 62/492,841, filed on May 1, 2017.

(51) Int. Cl.
| | | |
|---|---|---|
| *A61K 31/137* | (2006.01) | |
| *A61K 9/00* | (2006.01) | |
| *A61K 9/06* | (2006.01) | |
| *A61K 31/404* | (2006.01) | |
| *A61K 31/48* | (2006.01) | |
| *A61K 45/06* | (2006.01) | |

(52) U.S. Cl.
CPC .......... *A61K 31/137* (2013.01); *A61K 31/404* (2013.01); *A61K 31/48* (2013.01); *A61K 9/0048* (2013.01); *A61K 9/06* (2013.01); *A61K 45/06* (2013.01)

(58) Field of Classification Search
CPC .............. A61K 31/404; A61K 31/4045; A61K 31/4439; A61K 31/48; A61K 31/522; A61K 31/7072; A61K 31/137; A61K 9/0048; A61K 9/06; A61P 27/02
See application file for complete search history.

(56) References Cited

U.S. PATENT DOCUMENTS

| | | | |
|---|---|---|---|
| 5,545,617 A | 8/1996 | Dartt et al. | |
| 5,925,677 A * | 7/1999 | Mano | A61K 31/00 |
| | | | 514/543 |
| 7,763,619 B2 * | 7/2010 | Collier, Jr. | A61K 31/519 |
| | | | 514/252.14 |
| 2006/0069124 A1 | 3/2006 | Rao et al. | |
| 2009/0191288 A1 | 7/2009 | Squires | |
| 2010/0016280 A1 | 1/2010 | Nichols et al. | |
| 2011/0104155 A1 | 5/2011 | Rekik | |
| 2012/0282242 A1 * | 11/2012 | Abreu | A61K 31/195 |
| | | | 514/288 |
| 2013/0040957 A1 | 2/2013 | Dhanoa | |
| 2013/0344049 A1 | 12/2013 | Foster et al. | |
| 2015/0118327 A1 | 4/2015 | Sewell | |
| 2015/0366915 A1 | 12/2015 | Gay et al. | |
| 2017/0020891 A1 | 1/2017 | Jensen | |

FOREIGN PATENT DOCUMENTS

WO    1996/14060    5/1996

OTHER PUBLICATIONS

Latkany, Current Opin., Ophthalmol., publ. 2008, vol. 19, pp. 287-291 (Year: 2008).*
5-hydroxytryptamine receptor 2A isoform 2 (GenBank Accession No. for amino acid sequence: NP _001159419.1), Mar. 15, 2020.
5-hydroxytryptamine receptor 2A isoform 2 (GenBank Accession No. for nucleotide sequence: NM_001165947.2), Mar. 8, 2020.
5-hydroxytryptamine receptor 2B isoform 2 (GenBank Accession No. for amino acid sequence; NP _001307687.1), May 9, 2021.
5-hydroxytryptamine receptor 2B isoform 2 (GenBank Accession No. for nucleotide sequence: NM_001320758.1), Feb. 25, 2019.
5-hydroxytryptamine receptor 2C isoform a precursor (GenBank Accession No. for amino acid sequence: NP_001243689.1), Oct. 11, 2020.
5-hydroxytryptamine receptor 2C isoform a precursor (GenBank: Accession No, for nucleotide sequence: NM_001256760.2), Oct. 11, 2020.
5-hydroxytryptamine receptor 2C isoform b precursor (GenBank Accession No. for amino acid sequence; NP_001243690.1), Oct. 11, 2020.
5-hydroxytryptamine receptor 2C isoform b precursor (GenBank Accession No. for nucleotide sequence: NM_001256761.2), Oct. 11, 2020.
Clement C, Capriotti JA, Kumar M, Hobden JA, Foster TP, Bhattacharjee PS, Thompson HW, Mahmud R, Liang B, Hill JM. Clinical and antiviral efficacy of an ophthalmic formulation of dexamethasone povidone-iodine in a rabbit model of adenoviral keratoconjunctivitis. Invest Ophthalmol Vis Sci. Jan. 21, 2011;52(1):339-44.
Collier, Robert J., et al. "Agonists at the serotonin receptor (5-HT1A) protect the retina from severe photo-oxidative stress." Investigative ophthalmology & visual science 52.5 (2011): 2118-2126.

(Continued)

*Primary Examiner* — Sarah Pihonak
(74) *Attorney, Agent, or Firm* — Baker Donelson

(57) ABSTRACT

This invention features compositions, methods, and kits for treating conditions associated with pathological ocular neovascularization, reducing scarring in the eye, treating dry eye, treating macular degeneration, and treating keratitis by administering a serotonin receptor agonist.

5 Claims, 21 Drawing Sheets
Specification includes a Sequence Listing.

(56) References Cited

OTHER PUBLICATIONS

Gennaro, A. (2000) "Remington: The Science and Practice of Pharmacy," 20th edition, Lippincott, Williams & Wilkins—Have the 2000 version, not 2005.

Green, W. Richard. "Histopathology of age-related macular degeneration." Mol Vis 5.27 (1999): 1-10.

Hill JM, Stern EM, Bhattacharjee PS, Malamud D, Clement C, Rodriguez P, Lukiw WJ, Ochoa AC, Foster TP, Velasco C, McFerrin HE Jr. The antimicrobial agent C31G is effective for therapy for HSV-1 ocular keratitis in the rabbit eye model. Antiviral Res. Oct. 2013;100(1):14-9.

HTR2A (5-hydroxytryptamine receptor 2A isoform 1 (Gen Bank Accession. No. for nucleotide sequence: NM_000621.4)), Mar. 8, 2020.

HTR2A (5-hydroxytryptamine receptor 2A isoform 1 (GenBankAccession No. for amino acid sequence: NP_000612.1)), Jul. 5, 2021.

HTR2B (5-hydroxytryptamine receptor 2B isoform 1 (GenBank Accession No, for amino acid sequence: NP_000858.3)), May 9, 2021.

HTR2B (5-hydroxytryptamine receptor 2B isoform 1 (GenBank Accession No. for nucleotide sequence: NM_000867.4), Jun. 23, 2013.

HTR2C (5-hydroxytryptamine receptor 2C isoform a precursor (GenBank Accession No, for amino acid sequence: NP_000859.1), Oct. 11, 2020.

HTR2C (5-hydroxytryptamine receptor 2C isoform a precursor (GenBank Accession No. for nucleotide sequence: NM_000868.3)), Oct. 11, 2020.

International Search Report for PCT/US2018/30448, dated Aug. 3, 3018.

Nichols, David E. "Structure-activity relationships of serotonin 5-HT2A agonists." Wiley Interdisciplinary Reviews: Membrane Transport and Signaling 1.5 (2012): 559-579.

Nichols, David E., and Charles D. Nichols. "Serotonin receptors." Chemical reviews 108.5 (2008): 1614-1641.

Rajasagi, Naveen K., et al. "Controlling herpes simplex virus-induced ocular inflammatory lesions with the lipid-derived mediator resolvin E1." The Journal of Immunology 186.3 (2011): 1735-1746.

Roth, Bryan L., et al. "5-Hydroxytryptamine2 receptors coupled to phospholipase C in rat aorta: modulation of phosphoinositide turnover by phorbol ester." Journal of Pharmacology and Experimental Therapeutics 238.2 (1986): 480-485.

Rowe, Raymond C., Paul Sheskey, and Marian Quinn. Handbook of pharmaceutical excipients. Libros Digitales—Pharmaceutical Press, 2009.

Written Opinion of the International Searching Authority for PCT/US2018/30448, dated Aug. 3, 2018.

May et al., Journal of Pharmacology and Experimental Therapeutics 306(1) 301-309 (2003).

Johnson et al., Neuropharmacology 26(12) 1803-1806 (1987).

McKenna et al., Brain research 476(1) 45-56 (1989).

Nazarali et al., Progress in Neuro-Psychopharmacology and Biological Psychiatry 13(3-4) 573-581 (1989).

Machida et al., Recent Advances in 5-Hydroxytryptamine (5-HT) Receptor Research: How Many Pathophysiological Roles Does 5-HT Play via Its Multiple Receptor Subtypes? Biol. Pharm. Bull., 2013, 36(9), 1416-1419.

* cited by examiner

| Treatment Group | Eyes Showing Clinical Signs of Disease | # Died | Clinically Clear Eyes |
|---|---|---|---|
| BSS Drops | 7/8 | 2/6 | 0/8 |
| 1% TFT | 7/10 | 0/5 | 0/10 |
| XTPFDOI | 3/10* | 0/5 | 6/10 |

*FIG. 3*

Consistent regular epithelium layer
Tight Corneal Stromal layer
No signs of inflammation or Vascularization

COMPOSITIONS AND METHODS FOR TREATING OCULAR PATHOLOGIES

This application is a National Stage Application under 35 U.S.C. section 371 of PCT/US18/30448 filed May 1, 2018, which claims priority from and the benefit of U.S. Provisional Application No. 62/492,841, filed on May 1, 2017, the contents of each application which are incorporated herein by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

STATEMENT REGARDING FEDERALLY SPONSORED RESEARCH

This invention was made with government support under Grant No. P30GM106392 awarded by the National Institutes of Health and Project No. 08-69-04921 awarded by the US Department of Commerce Economic Development Administration. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Physiological angiogenesis and neovascularization processes are important for embryonic development, tissue remodeling, and wound healing. However, in certain tissues and diseases, such as the eye, dysregulation of these tightly controlled processes can result in vascularization-mediated pathological conditions. Pathological ocular neovascularization and dysregulation of vascular function can lead to and result from various conditions, including stromal keratitis, proliferative retinopathies, and macular degeneration, which generate substantial health complications.

There is a need in the field to develop effective therapies for treatment of conditions associated with pathological ocular neovascularization.

SUMMARY OF THE INVENTION

The invention provides compositions, methods, and kits for treating conditions associated with pathological ocular neovascularization, reducing scarring in the eye, treating dry eye, treating macular degeneration, and treating keratitis in a subject (e.g., a mammal, e.g., a human subject).

In one aspect, the invention features a method of treating a condition associated with pathological ocular neovascularization (e.g., a corneal neovascularization or a choroidal neovascularization). Such methods include administering to a subject in need thereof a therapeutically effective amount of a serotonin receptor agonist (e.g., a 5-$HT_{2A}$ receptor agonist, e.g., DOI (±)-1-(2,5-dimethoxyphenyl)-2-aminopropane hydrochloride; (R)-DOI ((R)-1-(2,5-dimethoxy-4-iodophenyl)-2-aminopropane) (greater than 95% R enantiomer); LA-SS-Az (2'S,4'S)-(+)-9,10-Didehydro-6-methylergoline-8 I 3-(trans-2,4-dimethylazetidide); 2C-BCB (4-Bromo-3,6-d imethoxybenzocyclobuten-1-yl) methylamine; or lysergic acid diethylamide (LSD)) in a pharmaceutically acceptable carrier or salt thereof. In some embodiments, conditions associated with pathological ocular neovascularization include, but are not limited to, macular degeneration (e.g., age-related macular degeneration), keratoconjunctivitis (adenoviral keratoconjunctivitis), conjunctivitis (adenoviral conjunctivitis), diabetic retinopathy, retinopathy of prematurity, polypoidal choroidal vasculopathy, ischemic proliferative retinopathy, retinitis pigmentosa, cone dystrophy, proliferative vitreoretinopathy, retinal artery occlusion, retinal vein occlusion, Leber's disease, retinal detachment, retinal pigment epithelial detachment, rubeosis iridis, corneal neovascularization, retinal neovascularization, choroidal neovascularization, retinochoroidal neovascularization, cancer (e.g., ocular cancer, e.g., retinoblastoma), or a combination thereof.

In another aspect, the invention provides a method of reducing scarring in the eye (e.g., scarring of the cornea or scarring associated with age-related macular degeneration (e.g., wet age-related macular degeneration)) by administering to a subject in need thereof a therapeutically effective amount of a serotonin receptor agonist (e.g., a 5-$HT_{2A}$ receptor agonist, e.g., DOI, R-DOI, or LSD) in a pharmaceutically acceptable carrier or salt thereof.

In another aspect, the invention features a method of treating dry eye (e.g., keratoconjunctivitis sicca) by administering to a subject in need thereof a therapeutically effective amount of a serotonin receptor agonist (e.g., a 5-$HT_{2A}$ receptor agonist, e.g., DOI, R-DOI, or LSD) in a pharmaceutically acceptable carrier or salt thereof.

In another aspect, the invention provides a method of treating macular degeneration (e.g., age-related macular degeneration (AMD)) by administering to a subject in need thereof a therapeutically effective amount of a serotonin receptor agonist (e.g., a 5-$HT_{2A}$ receptor agonist, e.g., DOI, R-DOI, or LSD) in a pharmaceutically acceptable carrier or salt thereof.

In another aspect, the invention provides a method of treating keratitis, the method comprising administering to a subject in need thereof a therapeutically effective amount of a serotonin receptor agonist (e.g., a 5-$HT_{2A}$ receptor agonist, e.g., DOI, R-DOI, or LSD) in a pharmaceutically acceptable carrier or salt thereof. In some embodiments, the keratitis is a viral keratitis (e.g., herpes keratitis).

In some embodiments of any of the preceding aspects, the serotonin receptor agonist is a 5-$HT_{2A}$ receptor agonist (e.g., DOI, R-DOI, or LSD). In some embodiments, the serotonin receptor agonist is a compound of formula (I), formula (II), or formula (III).

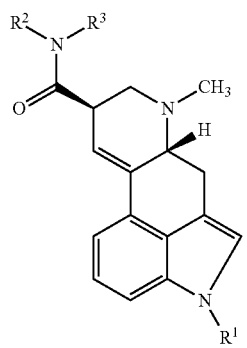

formula (I)

-continued

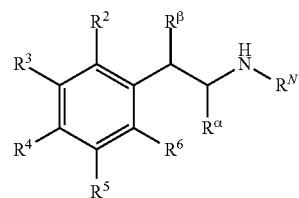
formula (II)

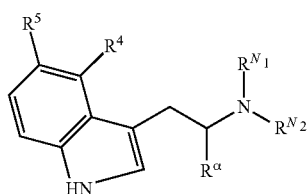
formula (III)

In some embodiments, the 5-$HT_{2A}$ receptor agonist is 2,5-Dimethoxy-4-iodoamphetamine (DOI). In other embodiments, the 5-$HT_{2A}$ receptor agonist is R-2,5-Dimethoxy-4-iodoamphetamine (R-DOI).

In some embodiments of any of the preceding methods, the serotonin receptor agonist is administered in combination with one or more additional therapeutic agents. For example, the one or more additional therapeutic agents may include an antibiotic agent, an antibacterial agent, an antiviral agent, an anti-inflammatory agent, an anti-VEGF agent, a corticosteroid, or a combination thereof. In some embodiments, the antiviral agent is trifluridine (TFT) or ganciclovir. In some embodiments, the serotonin receptor agonist (e.g., a 5-$HT_{2A}$ receptor agonist, e.g., DOI, R-DOI, or LSD) is administered at a different time from the additional therapeutic agent. In other embodiments, the serotonin receptor agonist (e.g., a 5-$HT_{2A}$ receptor agonist, e.g., DOI, R-DOI, or LSD) is administered concurrently with the additional therapeutic agent. In some embodiments, the serotonin receptor agonist is administered to the eye (e.g., as an ocular formulation). For example, the serotonin receptor agonist can be administered ocularly (e.g., by topical administration (e.g., by eye drop administration, gel administration, or ointment administration), instillation in the conjunctival sac, intravitreal administration, subconjunctival administration, retrobulbar administration, intracameral administration, or sub-Tenon's administration). In some embodiments, the serotonin receptor agonist is administered systemically.

The subject of any of the preceding aspects can be a mammal (e.g., a human, e.g., a human having a condition associated with pathogenic ocular neovascularization, e.g., a human having macular degeneration (e.g., age-related macular degeneration), keratoconjunctivitis, conjunctivitis, keratitis, diabetic retinopathy, retinopathy of prematurity, polypoidal choroidal vasculopathy, ischemic proliferative retinopathy, retinitis pigmentosa, cone dystrophy, proliferative vitreoretinopathy, retinal artery occlusion, retinal vein occlusion, Leber's disease, retinal detachment, retinal pigment epithelial detachment, rubeosis iridis, corneal neovascularization, retinal neovascularization, choroidal neovascularization, retinochoroidal neovascularization, or a combination thereof).

In another aspect, the invention features a pharmaceutical composition comprising a serotonin receptor agonist and an antiviral agent. In some embodiments, the serotonin receptor agonist is a compound of formula (I), formula (II), or formula (III).

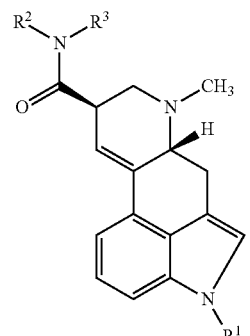
formula (I)

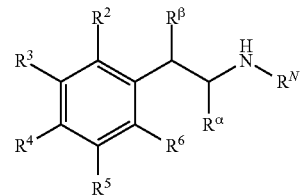
formula (II)

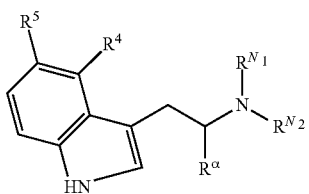
formula (III)

In some embodiments, the 5-$HT_{2A}$ receptor agonist is 2,5-Dimethoxy-4-iodoamphetamine (DOI). In other embodiments, the 5-$HT_{2A}$ receptor agonist is R-2,5-Dimethoxy-4-iodoamphetamine (R-DOI).

In some embodiments, the antiviral agent is TFT, acyclovir, gancyclovir, penciclovir, famiciclovir, cidofovir, cidofovir analog derivatives, ribavirin, interferon, phosphonoacetate, foscarnet, fomivirsen, or valganciclovir.

In another aspect, the invention provides a kit comprising the pharmaceutical composition comprising a serotonin receptor agonist and an antiviral agent. In some embodiments, the serotonin receptor agonist is a 5-$HT_{2A}$ receptor agonist. In some embodiments, the serotonin receptor agonist is a compound of formula (I), formula (II), or formula (III).

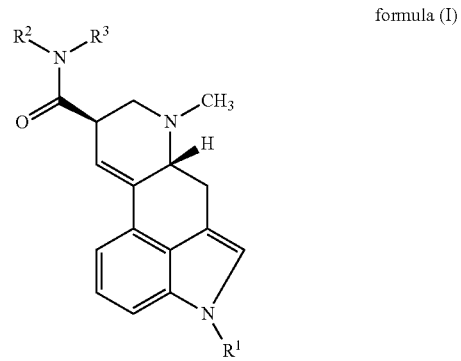
formula (I)

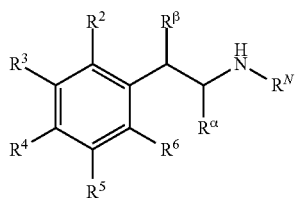

formula (II)

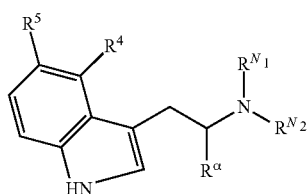

formula (III)

In some embodiments, the 5-HT$_{2A}$ receptor agonist is 2,5-Dimethoxy-4-iodoamphetamine (DOI). In other embodiments, the 5-HT$_{2A}$ receptor agonist is R-2,5-Dimethoxy-4-iodoamphetamine (R-DOI). In some embodiments, the antiviral agent of the kit is TFT, acyclovir, gancyclovir, penciclovir, famiciclovir, cidofovir, cidofovir analog derivatives, ribavirin, interferon, phosphonoacetate, foscarnet, fomivirsen, or valganciclovir.

Definitions

The singular forms "a", "an" and "the" include plural reference unless the context dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is consistent with the common United States patent law definition of "comprising" and is understood to have an open term meaning "at least the following," and also does not exclude additional features, limitations, aspects, etc. Wherever the terms "a" or "an" are used, "one or more" is understood, unless it is nonsensical in context.

As used herein, "about" refers to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

A "compound of the invention" as used herein encompasses, for example, a compound of formula (I), a compound of formula (II), a compound of formula (III), and any subgenera and/or species thereof. In embodiments, the serotonin receptor agonist comprises an agonist with at least one Phenethylamine group, an agonist with at least one Tryptamine group, or an agonist with at least one Ergoline group.

Non-limiting examples of an agonist that comprises a Phenethylamine group include 1-(4-Iodo-2,5-dimethoxyphenyl)propan-2-amine (DOI; also referred to as 2,5-Dimethoxy-4-iodoamphetamine), 1-(4-bromo-2,5-dimethoxyphenyl)propan-2-amine (DOB), 1-(4-methyl-2,5-d imethoxyphenyl)propan-2-amine (DOM), 1-(2,5-Dimethoxy-4-nitrophenyl)propan-2-amine (DON), 2-(4-Iodo-2,5-dimethoxyphenyl)ethan-1-amine (2 CI), 4-Bromo-2,5-dimethoxyphenylethanamine (2CB), 1-(3,4,5-Trimethoxyphenyl)propan-2-amine (TMA), 2-(3,4,5-trimethoxyphenyl)ethanamine (Mescaline), 1-[2,5-Dimethoxy-4-(trifluoromethyl)phenyl]propan-2-amine (DOTFM), (8R)-1-[(2S)-2-aminopropyl]-8,9-dihydro-7H-pyrano[2,3-g]indazol-8-ol (Alcon #13), (2R)-1-[4-(trifluoromethyl)-2,3,6,7-tetrahydrofuro[2,3-f][1]benzofuran-8-yl]propan-2-amine (TFMFly), and 25CINMoMe. Non-limiting examples of an agonist that comprises a Tryptamine group includes DMT, [3-(2-Dimethylaminoethyl)-1H-indol-4-yl] dihydrogen phosphate (Psilocybin), 3-[2-(Dimethylamino)ethyl]-1H-indol-4-ol (Psilocin), and 5MEO-DMT. In some embodiments, the serotonin receptor agonist is an indazole compound, such as (S)-2-(8,9-dihydro-7H-pyrano[2,3-g]indazol-1-yl)-1-methylethylamine (AL-38022A). Non-limiting examples of an agonist that comprises an Ergoline group includes 6aR,9R)-N,N-diethyl-7-methyl-4,6,6a,7,8,9-hexahydroindolo-[4,3-fg]quinoline-9-carboxamide (LSD), 1,1-Diethyl-3-(7-methyl-4,6,6a,7,8,9-hexahydro-indolo[4,3-fg]quinolin-9-yl)-urea (Lisuride), and (6aR,9R)-5-bromo-N,N-diethyl-7-methyl-4,6,6a,7,8,9-hexahydroindolo[4,3-fg]quinoline-9-carboxamide (Bromo-LSD; BOL). In some embodiments, the serotonin receptor agonist comprises 1-(4-Iodo-2,5-dimethoxyphenyl)propan-2-amine (DOI; also referred to as 2,5-Dimethoxy-4-iodoamphetamine).

An "effective amount", "sufficient amount" or "therapeutically effective amount" refers to an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

As is understood in the art, "treating" or "treatment" refers to an approach for obtaining beneficial or desired results, including clinical results. Beneficial or desired clinical results can include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also be prolonging survival as compared to expected survival if not receiving treatment. The effect of treatment can include reversing, alleviating, reducing severity of, curing, inhibiting the progression of, and/or reducing the likelihood of recurrence of the disease or one or more symptoms or manifestations of the disease.

The term "in need thereof" refers to the need for symptomatic or asymptomatic relief from a condition (e.g., a condition associated with a pathological ocular neovascularization). The subject in need thereof may or may not be undergoing treatment for conditions related to.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, $21^{st}$ Edition (University of the Sciences in Philadelphia, ed., Lippincott Williams & Wilkins 2005); and Handbook of Pharmaceutical Excipients, 7th Edition (Raymond Rowe et al., ed., Pharmaceutical Press 2012); each hereby incorporated by reference in its entirety.

The terms "animal," "subject," and "patient" refer to all members of the animal kingdom including, but not limited to, mammals, animals (e.g., cats, dogs, cows, horses, swine, etc.) and humans.

"Ocular tissue" refers to a tissue contained within the eye. Ocular tissues includes tissues comprising cells of the lens, the cornea (e.g., endothelial, stromal and/or epithelial corneal cells), the iris, the retina, choroid, sclera, ciliary body, vitrous body, ocular vasculature, canal of Schlemm, ocular muscle cells, optic nerve, and other ocular sensory, motor and autonomic nerves).

"Ocular disease" refers to a disease or condition of the eye ora tissue of the eye, including but not limited to, macular degeneration (e.g., age-related macular degeneration; AMD), choroidal vascularization, diabetic retinopathies, viral retinopathies, glaucoma, corneal allograft transplant rejection, ocular hypertension, corneal neovascularization, keratoconjunctivitis, viral conjunctivitis, keratoconjunctivitis, allergic conjunctivitis, uveitis, iritis, keratitis, infection, and cancer.

"Symptoms" refer to biological and/or physiological sequelae, including but not limited to hypersensitivity, burning, itching and light sensitivity, decrease in visual acuity, redness, pain, irritation, and photophobis.

"Agonist" refers to a compound that can combine with a receptor, such as a serotonin receptor, to produce a cellular response. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular serotonin receptor, such as a $5-HT_{2A}$ serotonin receptor agonist.

BRIEF DESCRIPTION OF THE FIGURES

FIG. 3 shows examining ability of DOI to control long-term chronic effects of HSV-mediated stromal keratitis: DAY 15 post infection. The three eyes in this group that had not clinically resolved disease, still had low clinical scores associated with their pathology as shown in the accompanying pathology.

FIG. 5 shows ocular histology of eyes from BalBc experiments examining ability of DOI to control long-term chronic effects of HSV-mediated stromal keratitis: DAY 15 post infection. HSV/RE Infected; Control BSS Treatment Drops.

FIG. 6 shows ocular histology of eyes from BalBc experiments examining ability of DOI to control long-term chronic effects of HSV-mediated stromal keratitis: DAY 15 post infection. HSV/RE Infected; Control 1% TFT Antiviral Treatment Drops.

DETAILED DESCRIPTION OF THE INVENTION

Figure 1:
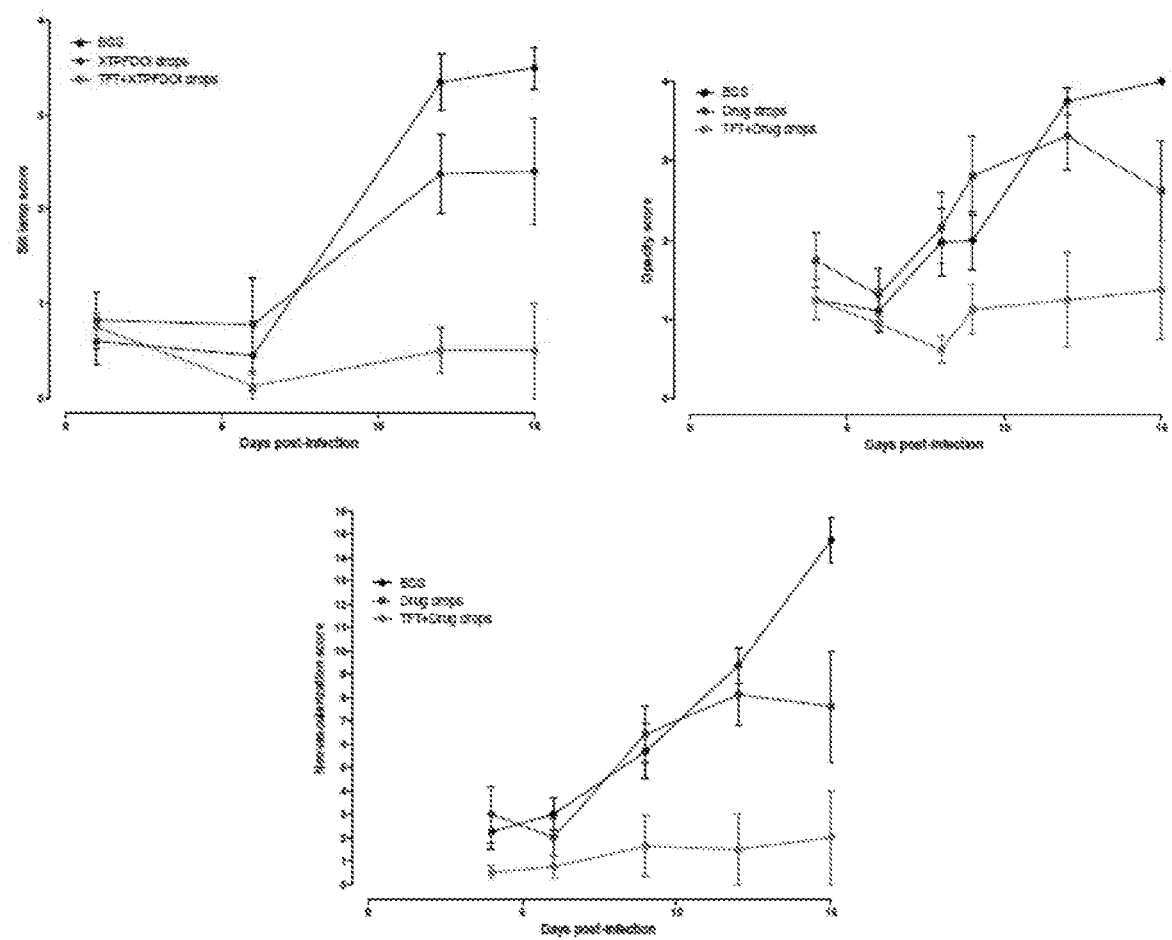
FIG. 1 shows the comparison of acute and chronic disease scores in C57Black mice following treatment with BS, XTPFDOI or 0.5% TFT+XTPFDOI. Treatment: 4 µl/eye/4× daily for 8 days (treatment duration did not exceed 8 days); Infection model Herpes Stromal Keratitis; C57Black; HSV-1 RE; 12,000 PFU/eye; Clinical Assessment Parameters Shown: Slit-Lamp Biomicroscopy of Eye; Stromal Opacity/Inflammation; Corneal Neovascularization

Detailed descriptions of one or more preferred embodiments are provided herein. However, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The invention provides means for treating or preventing ocular conditions (e.g., conditions associated with any region of the eye, such as the cornea, retina, iris, uvea, conjunctiva, and macula). In particular, methods and compositions of the invention may treat conditions associated with pathological ocular neovascularization (e.g., conjunctivitis), to reduce scarring in the eye, to treat dry eye, to treat macular degeneration (e.g., age-related macular degeneration), and/or to treat keratitis (e.g., herpes keratitis). The invention is based, at least in part, on the discovery disclosed herein that agonists of the serotonin receptor (e.g., the $5\text{-}HT_{2A}$ receptor) can be useful in (a) treating conditions associated with pathological ocular neovascularization; (b), reducing scarring in the eye; (c) treating dry eye; (d) treating macular degeneration; and/or (e) treating keratitis (e.g., herpes keratitis), e.g., by inhibiting pathological neovascularization (e.g., angiogenesis and or lymphangiogenesis).

Serotonin and the $5\text{-}HT_{2A}$ Receptor

Serotonin (5 hydroxytryptamine; 5-HT) is a neurotransmitter and hormone whose effects are mediated through interactions at seven different families of receptor proteins, comprised of 14 different subtypes, consisting of 13 G-protein coupled receptors and one ligand-gated ion channel. Embodiments as described herein can comprise any of the receptor proteins of the seven different families of receptor proteins.

Serotonin is primarily known for its function as a neurotransmitter within the CNS and is involved in many processes, including cognition and memory. In the periphery, however, serotonin also mediates processes, such as vasoconstriction (e.g., through the serotonin receptor $5\text{-}HT_{2A}$).

In some embodiments of the invention described herein, the invention involves activation of $5\text{-}HT_{2A}$ in the eye. In other embodiments, the serotonin receptor comprises other receptor proteins of the family of serotonin receptors, such as $5\text{-}HT_{2B}$ and $5\text{-}HT_{2C}$ receptors, or downstream effector proteins activated by serotonin $5\text{-}HT_{2A}$ receptors that convey the therapeutic effect to the cell or tissue.

Ocular Conditions

The term "ocular condition" can refer to a disease or condition of one or more tissues, parts, or ocular regions of the eye that impairs the normal functioning of the eye. The anterior segment of the eye refers to the front third of the eyeball and includes structures located between the front surface of the cornea and the vitreous. The posterior segment of the eye refers to the rear two-thirds of the eyeball (behind the lens) and includes the vitreous, retina, optic disc, choroid, and pars plana.

The "eye" is the sense organ for sight, and includes the eyeball, or globe, the orbital sense organ that receives light and transmits visual information to the central nervous system. Broadly speaking, the eye includes the eyeball and the tissues and fluids which constitute the eyeball, the periocular muscles (such as the oblique and rectus muscles), and the portion of the optic nerve which is within or adjacent to the eyeball.

Physiological angiogenesis, neovascularization, and a normal immune system are required for embryonic development, tissue remodeling and wound healing. However, in certain tissues and diseases, dysregulation of these tightly controlled processes can result in pathological conditions, such as ocular conditions.

Pathological vascularization, dysregulation of vascular function, and hypersensitivity are critical determinates in the outcome of many ocular diseases and pathologies. For example, pathological vascularization is a critical component to blinding stromal keratitis, proliferative retinopathies, and macular degeneration (e.g., age-related macular degeneration). Embodiments as described herein can treat conditions or symptoms of ocular vascularization-associated disease processes, such as in macular degeneration (e.g., age-related macular degeneration), keratoconjunctivitis, conjunctivitis, diabetic retinopathy, retinopathy of prematurity, polypoidal choroidal vasculopathy, ischemic proliferative retinopathy, retinitis pigmentosa, cone dystrophy, proliferative vitreoretinopathy, retinal artery occlusion, retinal vein occlusion, Leber's disease, retinal detachment, retinal pigment epithelial detachment, rubeosis iridis, corneal neovascularization, retinal neovascularization, choroidal neovascularization, retinochoroidal neovascularization, keratitis, or a combination thereof.

In diseases of the eye, pathological vascularization is associated with exacerbation of the pathological processes within the innervated tissue and lowers the prognosis of disease resolution. Development of in vitro and in vivo vascularization-associated disease model systems have been expanded to additional pathological vascularization-associated diseases and provided opportunities to evaluate additional therapeutics, including serotonin receptor agonists such as the serotonin (5-HT) agonist 2,5-Dimethoxy-4-iodoamphetamine (DOI). Findings indicate that in ocular models of disease, DOI potently inhibits disease-associated vascularization of tissues, thereby preventing the chronic pathology normally associated with disease progression.

Embodiments as described herein can be used to treat or ameliorate the symptoms associated with diseases of the eye. For example, dysregulation of vascularization processes or hypersensitivity can lead to vision-threatening ocular diseases or pathologies. In embodiments, a vascular-associated eye disease or hypersensitivity can be associated with, is caused by, or is exacerbated by vascular defects including but not limited to, angiogenesis, lymphangiogenesis, neovascularization, vascular leakage, edema, increased oxygen, ischemia, vasoconstriction, vasodilation, hemorrhaging, vascular occlusions, increased hypersensitivity reactions and/or ocular hypertension. Non-limiting examples of ocular diseases, such as vascularization-associated diseases of the eye, include macular degeneration (e.g., age-related macular degeneration), keratoconjunctivitis (e.g., adenoviral keratoconjunctivitis), conjunctivitis (e.g., adenoviral conjunctivitis), diabetic retinopathy, retinopathy of prematurity, polypoidal choroidal vasculopathy, ischemic proliferative retinopathy, retinitis pigmentosa, cone dystrophy, proliferative vitreoretinopathy, retinal artery occlusion, retinal vein occlusion, Leber's disease, retinal detachment, retinal pigment epithelial detachment, rubeosis iridis, corneal neovascularization, retinal neovascularization, choroidal neovascularization, retinochoroidal neovascularization, keratitis.

In some embodiments, the present invention provides compositions, methods, and kits for treating dry eye (e.g., keratoconjunctivitis sicca).

The compositions, methods, and kits of the invention can also be used to reduce, or ameliorate, or prevent scarring of the eye (e.g., scarring of the cornea, or scarring resulting from macular degeneration, e.g., age-related macular degeneration, e.g., wet age-related macular degeneration).

Keratitis

The present invention provides compositions, methods, and kits that can be used to reduce, or ameliorate, or prevent keratitis, non-limiting examples of which are described herein.

In some embodiments, keratitis may be associated with an infection that may be fully resolved. In other embodiments, the infection may never be resolved, such as is the case with a herpes viral infection. For example, replication at the initial site of infection can be resolved, but the infection persists within a state of latency with sporadic episodes of reinfection. It can be important to control the recurrent nature of a lifelong infection that reactivates from neurons to cause repeated bouts of ocular disease as seen in chronic herpetic eye disease. Embodiments as described herein can control reactivation-mediated recurrent disease.

Embodiments as described herein can prevent reactivation of a latent virus, so as to prevent viral shedding, transmission, sporadic reinfection of tissues, subsequent recurrent acute disease, and development of chronic disease manifestations.

Viral Retinopathy

"Retinopathy" can refer to a persistent or acute damage to the retina of the eye. In certain instances, the damage to the retina of the eye can cause loss of function of the eye. In certain instances, hypersensitivity and vascular remodeling can occur over prolonged periods of time unnoticed by the subject suffering from the pathology.

Retinopathies can be caused by diabetes mellitus, arterial hypertension, retinopathy of prematurity, radiation retinopathy, solar retinopathy, sickle cell disease, retinal vascular disease such as retinal vein or artery occlusion, trauma, or an infection, such as a viral infection (e.g., herpes keratitis). In embodiments, the retinopathies are viral retinopathies, and can be Cytomegalovirus (CMV)- or Varicella-Zoster Virus (VZV)-associated.

Retinopathies are often proliferative, and can result from neovascularization.

Viral retinopathies comprise CMV-associated retinopathies, such as CMV retinitis, and VZV-associated retinopathies.

Cytomegalovirus is a ubiquitous DNA virus that infects the majority of the adult population. In the immunocompetent host, infection can be asymptomatic or limited to a mononucleosis-like syndrome. Like many other herpesviruses, CMV remains latent in the host and may reactivate if host immunity is compromised.

In immunocompromised individuals, primary infection or reactivation of latent virus can lead to opportunistic infection of multiple organ systems. In the eye, CMV most commonly presents as a viral necrotizing retinitis. If left untreated, CMV retinitis inexorably progresses to visual loss and blindness.

Diabetic Retinopathy

"Diabetic retinopathy" can refer to damage to the retina or disorders of the retina that is caused by diabetes. For example, the damage can be to the blood vessels in the retina of the eye which are vital to bringing oxygen and nutrients to the retina.

Diabetic retinopathy is the third leading cause of adult blindness (accounting for almost 7% of blindness in the USA), is associated with extensive angiogenic events. Nonproliferative retinopathy is accompanied by the selective loss of pericytes within the retina, and their loss results in dilation of associated capillaries dilation and a resulting increase in blood flow. In the dilated capillaries, endothelial cells proliferate and form outpouchings, which become microaneurysms, and the adjacent capillaries become blocked so that the area of retina surrounding these microaneurysms is not perfused. Eventually, shunt vessels appear between adjacent areas of micro aneurysms, and the clinical picture of early diabetic retinopathy with micro aneurysms and areas of nonperfused retina is seen. The microaneurysms leak and capillary vessels may bleed, causing exudates and hemorrhages. Once the initial stages of background diabetic retinopathy are established, the condition progresses over a period of years, developing into proliferative diabetic retinopathy and blindness in about 5% of cases. Proliferative diabetic retinopathy occurs when some areas of the retina continue losing their capillary vessels and become nonperfused, leading to the appearance of new vessels on the disk and elsewhere on the retina. These new blood vessels grow into the vitreous and bleed easily, leading to preretinal hemorrhages. In advanced proliferative diabetic retinopathy, a massive vitreous hemorrhage may fill a major portion of the vitreous cavity. In addition, the new vessels are accompanied by fibrous tissue proliferation that can lead to traction retinal detachment.

Diabetic retinopathy is associated primarily with the duration of diabetes mellitus. Therefore, as the population ages and diabetic patients live longer, the prevalence of diabetic retinopathy will increase. Laser therapy is currently used in both nonproliferative and proliferative diabetic retinopathy. Focal laser treatment of the leaking microaneurysms surrounding the macular area reduces visual loss in 50% of patients with clinically significant macular edema. In proliferative diabetic retinopathy, panretinal photocoagulation results in several thousand tiny burns scattered throughout the retina (sparing the macular area); this treatment reduces the rate of blindness by 60%. Early treatment of macular edema and proliferative diabetic retinopathy prevents blindness for 5 years in 95% of patients, whereas late treatment prevents blindness in only 50 percent. Therefore, early diagnosis and treatment are essential.

Age-Related Macular Degeneration

"Macular degeneration" can refer to the degeneration of the macula, a small yellow area on the back of the eye and located in the middle of the retina. Because of the position of the macula (the center of the retina), the resulting vision loss in macular degeneration is the central vision. In many cases, people suffering from age-related macular degeneration have normal peripheral vision, but generate a blind spot right in the middle of their sight path. Therefore, macular degeneration can affect one's ability to read, drive and recognize faces.

Age-related macular degeneration (AMD), a disease that affects approximately one in ten Americans over the age of 65, is characterized by a series of pathological changes in the macula, the central region of the retina, which is accompanied by decreased visual acuity, particularly affecting central vision. AMD involves the single layer of cells called the retinal pigment epithelium that lies immediately beneath the sensory retina. These cells nourish and support the portion of the retina in contact with them, i.e., the photoreceptor cells that contain the visual pigments. The retinal pigment epithelium lies on the Bruch membrane, a basement membrane complex which, in AMD, thickens and becomes sclerotic. New blood vessels may break through the Bruch membrane from the underlying choroid, which contains a rich vascular bed. These vessels may in turn leak fluid or bleed beneath the retinal pigment epithelium and also between the retinal pigment epithelium and the sensory retina. Subsequent fibrous scarring disrupts the nourishment of the photoreceptor cells and leads to their death, resulting in a loss of central visual acuity. This type of age-related maculopathy is called the "wet" type because of the leaking vessels and the subretinal edema or blood. The wet type accounts for only 10% of age-related maculopathy cases but results in 90% of cases of legal blindness from macular degeneration in the elderly. The "dry" type of age-related maculopathy involves disintegration of the retinal pigment epithelium along with loss of the overlying photoreceptor cells. The dry type reduces vision but usually only to levels of 20/50 to 20/100.

AMD is accompanied by distortion of central vision with objects appearing larger or smaller or straight lines appearing distorted, bent, or without a central segment. In the wet type of AMD, a small detachment of the sensory retina may be noted in the macular area, but the definitive diagnosis of a subretinal neovascular membrane requires fluorescein angiography. In the dry type, drusen may disturb the pigmentation pattern in the macular area. Drusen are excrescences of the basement membrane of the retinal pigment epithelium that protrude into the cells, causing them to bulge anteriorly; their role as a risk factor in age-related maculopathy is unclear. No treatment currently exists for the dry type of age-related maculopathy. Laser treatment is used in the wet type of age-related maculopathy and initially obliterates the neovascular membrane and prevents further visual loss in about 50% of patients at 18 months. By 60 months, however, only 20% still have a substantial benefit.

Pathogenesis

Pathogenesis can refer to the mode of origin, biological mechanism(s), or development of disease or condition. For example, pathogenesis can refer to hypersensitivity, angiogenesis, for example of blood vessels or lymphatic vessels; vascularization; vascular occlusions; vascular leakage; vascular permeability; angiogenesis; lymphangiogenesis; neovascularization; vasodialation; vasoconstriction, for example that of lymphatics or blood vessels; vascular occlusions; edema; corneal epithelial defects; increased intraocular pressure; increased oxygen saturation; ischemia; hemorrhage; necrotizing inflammation; epithelial hyperproliferation; epithelial thickening; fibrosis; or a combination thereof.

The present invention provides methods and compositions to treat conditions associated with vascular pathologies in the eye, including pathologies associated with aberrant blood neovascularization and lymph neovascularization (e.g., angiogenesis and lymphangiogenesis). Ocular conditions associate with pathological neovascularization include macular degeneration (e.g., age-related macular degeneration), keratoconjunctivitis (e.g., adenoviral keratoconjunctivitis), conjunctivitis (e.g., adenoviral conjunctivitis), diabetic retinitis, retinopathy of prematurity, polypoidal choroidal vasculopathy, ischemic proliferative retinopathy, retinitis pigmentosa, cone dystrophy, proliferative vitreoretinopathy, retinal artery occlusion, retinal vein occlusion, Leber's disease, retinal detachment, retinal pigment epithelial detachment, rubeosis iridis, corneal neovascularization, retinal neovascularization, choroidal neovascularization, retinochoroidal neovascularization, or a combination thereof.

Embodiments of the invention described herein can reduce, ameliorate, or prevent conditions associated with pathogenesis of an ocular disease. In some embodiments, the pathogenesis is chronic pathogenesis, and persists after the acute disease itself is resolved. Non-limiting examples of ocular pathogenesis comprise hypersensitivity, angiogenesis, neovascularization, vascular leakage, vascular permeability, or a combination thereof.

Pathological vascularization and dysregulation of vascular function are main contributors to all infectious and many non-infectious disease processes in ocular tissue. Embodiments as described herein can be used to reduce, ameliorate, or inhibit vascularization, such as neovascularization, in an ocular tissue of a subject.

Embodiments as described herein can reduce, ameliorate or prevent symptoms associated with vascularization in an ocular tissue of a subject. Non-limiting examples of such symptoms comprise conjunctivitis, keratoconjunctivitis, ocular hypertension, glaucoma, macular degeneration, or edema.

In embodiments, the vascularized tissue can comprise a tissue of the eye.

In embodiments, neovascularization can refer to any type of angiogenesis or new vascularization of tissues. For example, vascularization can refer to angiogenesis of a blood vessel, angiogenesis of a lymphatic vessel, or a combination thereof.

Lymphangiogenesis plays key roles in regulating hypersensitivity, tissue edema, intraocular pressure, and hypersensitivity disease processes.

Non-limiting markers of vascularization and/or lymphangiogenesis comprise LYVE, VEGFA, VEGFB, VEGFC, VEGFD, VEGFR-3, PROX1, CCL21, TNF, IL-6, Angiopioetin 1, Angiopioetin 2, FLT-1, KDR, Tie-1, HIF1a, PGF, FGF, IL8, IL1B, IFN, TGF, IL17, TIMP, MMP2, MMP9, and NOTCH. In embodiments, neovascularization can be scored on a grading scale. For example, a three point scale can be used in a rabbit model, and a 16 point scale can be used in mice. Such scales allow for more accuracy in the assessment of neovascularization. For example, corneal neovascularization can be evaluated as previously described in Rajasagi et al. (2011; *J Immunol* 186:1735, which is incorporated herein in its entirety) using a scale of 0 to 16, where each of the four quadrants of the eye was evaluated for the density of vessels that have grown onto the cornea and the extent of neovessels. According to this system, the score of the four quadrants of the eye (between 0, indicating the absence of vessels, to 4, meaning maximal density of new vasculature) were then summed to derive the neovascularization index (a total range of 0-16) for each eye at a given time point.

Embodiments as described herein can be used to reduce, prevent, or ameliorate ocular hypersensitivity. Hypersensitivity refers to a localized protective reaction of tissue to irritation, injury, infection, or disease, and is characterized by pain, redness, swelling, and potentially loss of function.

Embodiments as described herein can be used to reduce, prevent, or ameliorate vascular leakage. Vascular leakage refers to the permeability of vessels and capillaries that can result in hypersensitivity of tissue, formation of edema, or leakage of blood cells into tissue. Vascular leakage can also be referred to as vascular permeability. Vascular leakage can be the one way flow of cells or fluid, or can be the two way flow of cells or fluid.

In embodiments, clinical diseases, for example stromal disease, corneal opacity, and ocular hypersensitivity, are scored according to a grading scale. For example, the scale can be a three point scale (from 0 to 3) and comprise the parameters that are documents in Hill et al. (*Antiviral Res.* 2013 October; 100(1):14-9) and Clement et al. (*Invest Ophthalmol Vis Sci.* 2011 Jan. 21; 52(1):339-44), both of which are incorporated herein in their entireties.

In embodiments, clinical scoring of slit lamp biomicroscopy can be visualized using a fluorophore enhance slit lamp biomicroscope. In embodiments, this can be scored on a grading scale, such as a 4 point scale (from 0 to 4), as detailed within Hill et al. (Antiviral Res. 2013 October; 100(1):14-9) and Clement et al. (*Invest Ophthalmol Vis Sci.* 2011 Jan. 21; 52(1):339-44), both of which are incorporated herein in their entireties.

Agonists

"Agonist" can refer to a compound that can combine and/or interact with a receptor, such as a serotonin receptor, to produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that said compound directly binds to the receptor. An agonist may be referred to as an agonist of a particular serotonin receptor, such as a 5-HT$_{2A}$ serotonin receptor agonist (e.g., DOI or R-DOI).

The term "5-HT$_{2A}$ agonists" can refer to any compound or ligand that increases the activity of a 5-hydroxytryptamine 2A receptor. Non-limiting examples of such agonists include, but are not limited to, DOI (±)-1-(2,5-dimethoxyphenyl)-2-aminopropane hydrochloride; (R)-DOI ((R)-1-(2,5-dimethoxy-4-iodophenyl)-2-aminopropane) (greater than 95% R enantiomer); LA-SS-Az (2'S,4'S)-(+)-9,10-Didehydro-6-methylergoline-8β-(trans-2,4-dimethylazetidide); 2C-BCB (4-Bromo-3,6-d imethoxybenzocyclobuten-1-yl) methylamine; and lysergic acid diethylamide (LSD).

Non-limiting examples of serotonin receptor agonists can be found in Nichols et al. (*WIREs Membr Transp Signal* 2012), which is incorporated herein in its entirety.

In embodiments, the serotonin receptor agonist can be a Phenethylamine, a Tryptamine, an Ergoline, or a combination thereof. Non-limiting examples of a Phenethylamine comprises 1-(4-Iodo-2,5-dimethoxyphenyl)propan-2-amine (DOI), 1-(4-bromo-2,5-dimethoxyphenyl)propan-2-amine (DOB), 1-(4-methyl-2,5-dimethoxyphenyl)propan-2-amine (DOM), 1-(2,5-Dimethoxy-4-nitrophenyl)propan-2-amine (DON), 2-(4-Iodo-2,5-dimethoxyphenyl)ethan-1-amine (2CI), 4-Bromo-2,5-dimethoxyphenylethanamine (2CB), 1-(3,4,5-Trimethoxyphenyl)propan-2-amine (TMA), 2-(3,4, 5-trimethoxyphenyl)ethanamine (Mescaline), 1-[2,5-Dimethoxy-4-(trifluoromethyl)phenyl]propan-2-amine (DOTFM), (2R)-1-[4-(trifluoromethyl)-2,3,6,7-tetrahydrofuro[2,3-f][1]benzofuran-8-yl]propan-2-amine (TFMFly), and 25CINMoMe.

Non-limiting examples of a Tryptamine comprises DMT, [3-(2-Dimethylaminoethyl)-1H-indol-4-yl] dihydrogen phosphate (Psilocybin), 3-[2-(Dimethylamino)ethyl]-1H-indol-4-ol (Psilocin), and 5MEO-DMT.

In embodiments, the serotonin receptor agonist is an indazole compound, such as (S)-2-(8,9-dihydro-7H-pyrano[2,3-g]indazol-1-yl)-1-methylethylamine (AL-38022A).

Non-limiting examples of an Ergoline comprises 6aR,9R)-N,N-diethyl-7-methyl-4,6,6a,7,8,9-hexahydroindolo-[4,3-fg]quinoline-9-carboxamide (LSD), 1,1-Diethyl-3-(7-methyl-4,6,6a,7,8,9-hexahydro-indolo[4,3-fg]quinolin-9-yl)-urea (Lisuride), and (6aR,9R)-5-bromo-N,N-diethyl-7-methyl-4,6,6a,7,8,9-hexahydroindolo[4,3-fg]quinoline-9-carboxamide (Bromo-LSD; BOL).

In embodiments, the composition comprises a compound having the following chemical formula

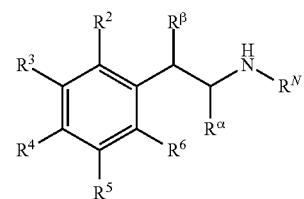

where non-limiting exemplary values of the R groups in the above substituted chemical structure are represented in Table 1, below:

TABLE 1

Exemplary R groups of a compound of formula (II).

| Name | $R^2$ | $R^3$ | $R^4$ | $R^5$ | $R^6$ | $R^\alpha$ | $R^\beta$ | $R^N$ |
|---|---|---|---|---|---|---|---|---|
| Mescaline | | $OCH_3$ | $OCH_3$ | $OCH_3$ | | | | |
| TMA | | $OCH_3$ | $OCH_3$ | $OCH_3$ | | $CH_3$ | | |
| TMA-2 | $OCH_3$ | | $OCH_3$ | $OCH_3$ | | $CH_3$ | | |
| methoxyDOB | $OCH_3$ | | Br | $OCH_3$ | | $CH_3$ | $OCH_3$ | |
| DOM | $OCH_3$ | | $CH_3$ | $OCH_3$ | | | | |
| DOB | $OCH_3$ | | Br | $OCH_3$ | | | | |
| DOI | $OCH_3$ | | I | $OCH_3$ | | | | |
| Sulfur analog of mescaline | | $OCH_3$ | $OCH_3$ | $SCH_3$ | | | | |
| Sulfur analog of mescaline | | $OCH_3$ | $SCH_3$ | $OCH_3$ | | | | |
| DOIB | $OCH_3$ | | $CH_2CH(CH_3)_2$ | $OCH_3$ | | $CH_3$ | | |
| DOTFM | $OCH_3$ | | $CF_3$ | $OCH_3$ | | $CH_3$ | | |

In some embodiments, $R^2$ of formula (II) can be OH, O—($C_1$-$C_6$-alkyl), —O—($C_2$-$C_6$-alkyl)-N($R^5$)$_2$, or —O—($C_2$-$C_6$-alkyl)-N(Rx)$_3$$^+$halogen$^-$; $R^3$ of formula (II) can be OH, O—($C_1$-$C_6$-alkyl), —O—($C_2$-$C_6$-alkyl)-N(Rx)$_2$, or —O—($C_2$-$C_6$-alkyl)-N(Rx)$_3$$^+$halogen$^-$; $R^4$ of formula (II)

can be halogen, $C_1$-$C_2$-haloalkyl, H, $C_1$-$C_6$-alkyl, $C_1$-$C_6$-alkyl sulfide, OH, O—($C_1$-$C_6$-alkyl), —O—($C_2$-$C_6$-alkyl)-N(Rx)$_2$, or —O—($C_2$-$C_6$-alkyl)-N(Rx)$_3$$^+$halogen$^-$; $R^5$ of formula (II) can be halogen, $C_1$-$C_2$-haloalkyl, H, $C_1$-$C_6$-alkyl, $C_1$-$C_6$-alkyl sulfide, OH, O—($C_1$-$C_6$-alkyl), —O—($C_2$-$C_6$-alkyl)-N(Rx)$_2$, or —O—($C_2$-$C_6$-alkyl)-N(Rx)$_3$$^+$halogen$^-$; $R^6$ of formula (II) can be halogen, $C_1$-$C_2$-haloalkyl, H, $C_1$-$C_6$-alkyl, —S—($C_1$-$C_6$-alkyl), OH, O—($C_1$-$C_6$-alkyl), —O—($C_2$-$C_6$-alkyl)-N($R^5$)$_2$, or —O—($C_2$-$C_6$-alkyl)-N($R^5$)$_3$$^+$halogen$^-$; $R^\alpha$ is H, halogen, or $C_1$-$C_6$-alkyl; $R^\beta$ of formula (II) can be OH, O—($C_1$-$C_6$-alkyl), —O—($C_2$-$C_6$-alkyl)-N($R^5$)$_2$, or —O—($C_2$-$C_6$-alkyl)-N(Rx)$_3$$^+$halogen$^-$; RN of formula (II) can be halogen, $C_1$-$C_2$-haloalkyl, H, $C_1$-$C_6$-alkyl, $C_1$-$C_6$-alkyl sulfide, OH, O—($C_1$-$C_6$-alkyl), —O—($C_2$-$C_6$-alkyl)-N(Rx)$_2$, or —O—($C_2$-$C_6$-alkyl)-N(Rx)$_3$$^+$halogen$^-$; and Rx is independently H or $C_1$-$C_4$-alkyl.

In embodiments, the composition comprises a compound having the following chemical formula (I):

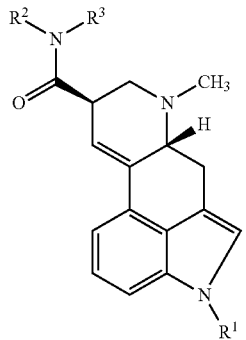

where the non-limiting exemplary values of the R groups in the above substituted chemical structure are represented Table 2, below:

TABLE 2

Exemplary R groups of a compound of formula (I).

| Name | $R^1$ | $R^2$ | $R^3$ |
|---|---|---|---|
| LSD | H | $CH_2CH_3$ | $CH_2CH_3$ |
| Ergine | H | H | H |
| R-2-butyl | H | H | $CH(CH_3)CH_2CH_3$ |
| R-2-pentylamine | H | H | $CH(CH_3)CH_2CH_2CH_3$ |
| Analog of ergine | H | $C_2H_5$ | H |
| Analog of ergine | H | H | $C_2H_5$ |
| LSD | H | $C_2H_5$ | $C_2H_5$ |
| Analog of ergine | H | $C_2H_5$ | $CH_2CH_2CH_3$ |
| Analog of ergine | H | $C_2H_5$ | $CH(CH_3)_2$ |
| Analog of ergine | H | $CH_2CH_2CH_3$ | H |
| Analog of ergine | H | H | $CH_2CH_2CH_3$ |
| Analog of ergine | H | $CH_2CH_2CH_3$ | $CH_2CH_2CH_3$ |
| Analog of ergine | H | $CH_2CH_2CH_3$ | $C_2H_5$ |
| Analog of ergine | H | $CH_2CH_2CH_3$ | $CH(CH_3)_2$ |
| Analog of ergine | H | $CH(CH_3)_2$ | H |
| Analog of ergine | H | H | $CH(CH_3)_2$ |
| Analog of ergine | H | $CH(CH_3)_2$ | $CH(CH_3)_2$ |
| Analog of ergine | H | $CH(CH_3)_2$ | $C_2H_5$ |
| Analog of ergine | H | $CH(CH_3)_2$ | $CH_2CH_2CH_3$ |

In some embodiments, $R^1$ of formula (I) can be H, $C_1$-$C_6$-alkyl, OH, O—($C_1$-$C_6$-alkyl), halogen, or $C_1$-$C_4$-haloalkyl; $R^2$ of formula (I) can be H, $C_1$-$C_6$-alkyl, OH, O—($C_1$-$C_6$-alkyl), halogen, or $C_1$-$C_4$-haloalkyl; and $R^3$ of formula (I) can be H, $C_1$-$C_6$-alkyl, OH, O—($C_1$-$C_6$-alkyl), halogen, or $C_1$-$C_4$-haloalkyl.

In embodiments, the composition comprises a compound having the following chemical formula (III):

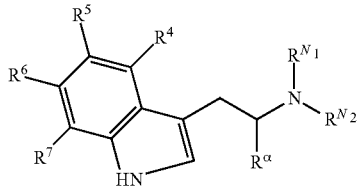

where the non-limiting exemplary values of the R groups in the above substituted chemical structure are represented in Table 3, below:

TABLE 3

Exemplary R groups of a compound of formula (III).

| Name | $R^{N1}$ | $R^{N2}$ | $R^\alpha$ | $R^4$ | $R^5$ | $R^6$ | $R^7$ |
|---|---|---|---|---|---|---|---|
| 6-fluoro-psilocin | C | C | H | OH | H | F | H |
| 7-fluoro-psilocin | C | C | H | OH | H | H | F |
| 4-fluoro-5-methoxy-DMT | C | C | H | F | $OCH_3$ | H | H |
| 6-fluoro-5-methoxy-DMT | C | C | H | H | $OCH_3$ | F | H |
| □-Methyl-tryptamine | H | H | $CH_3$ | H | H | H | H |
| Serotonin | H | H | H | H | OH | H | H |

In some embodiments, $R^{N1}$ of formula (III) can be H, $C_1$-$C_6$-alkyl, OH, O—($C_1$-$C_6$-alkyl), halogen, or $C_1$-$C_4$-haloalkyl; $R^{N2}$ of formula (III) can be H, $C_1$-$C_6$-alkyl, OH, O—($C_1$-$C_6$-alkyl), halogen, or $C_1$-$C_4$-haloalkyl; $R^\alpha$ of formula (I) can be H, $C_1$-$C_6$-alkyl, OH, O—($C_1$-$C_6$-alkyl), halogen, or $C_1$-$C_4$-haloalkyl; $R^4$ of formula (I) can be H, $C_1$-$C_6$-alkyl, OH, O—($C_1$-$C_6$-alkyl), halogen, or $C_1$-$C_4$-haloalkyl; $R^5$ of formula (I) can be H, $C_1$-$C_6$-alkyl, OH, O—($C_1$-$C_6$-alkyl), halogen, or $C_1$-$C_4$-haloalkyl; $R^6$ of formula (I) can be H, $C_1$-$C_6$-alkyl, OH, O—($C_1$-$C_6$-alkyl), halogen, or $C_1$-$C_4$-haloalkyl; and $R^7$ of formula (I) can be H, $C_1$-$C_6$-alkyl, OH, 0-($C_1$-$C_6$-alkyl), halogen, or $C_1$-$C_4$-haloalkyl.

In some embodiments, a compound of the invention (for example a compound of formula (I), (II), or (III)) binds to a serotonin receptor in a subject. Non-limiting examples of serotonin receptors include HTR2A (5-hydroxytryptamine receptor 2A isoform 1 (GenBank Accession No. for nucleotide sequence: NM_000621.4 and GenBank Accession No. for amino acid sequence: NP_000612.1); 5-hydroxytryptamine receptor 2A isoform 2 (GenBank Accession No. for nucleotide sequence: NM_001165947.2 and GenBank Accession No. for amino acid sequence: NP_001159419.1)); HTR2B (5-hydroxytryptamine receptor 2B isoform 1 (GenBank Accession No. for nucleotide sequence: NM_000867.4 and GenBank Accession No. for amino acid sequence: NP_000858.3); 5-hydroxytryptamine receptor 2B isoform 2 (GenBank Accession No. for nucleotide sequence: NM_001320758.1 and GenBank Accession No. for amino acid sequence: NP_001307687.1)); and HTR2C (5-hydroxytryptamine receptor 2C isoform a precursor (GenBank Accession No. for nucleotide sequence: NM_000868.3 and GenBank Accession No. for amino acid sequence: NP_000859.1); 5-hydroxytryptamine receptor 2C isoform a precursor (GenBank Accession No. for nucleotide sequence:

NM_001256760.2 and GenBank Accession No. for amino acid sequence: NP_001243689.1); 5-hydroxytryptamine receptor 2C isoform b precursor (GenBank Accession No. for nucleotide sequence: NM_001256761.2 and GenBank Accession No. for amino acid sequence: NP_001243690.1)).

In some embodiments, the serotonin receptor comprises SEQ ID NO: 1 (amino acids 1-481 having GenBank Accession No. NP_000858.3):

MALSYRVSELQSTIPEHILQSTFVHVISSNWSGLQTESIPEEMKQIVEEQ

GNKLHWAALLILMVIIPTIGGNTLVILAVSLEKKLQYATNYFLMSLAVAD

LLVGLFVMPIALLTIMFEAMWPLPLVLCPAWLFLDVLFSTASIMHLCAIS

VDRYIAIKKPIQANQYNSRATAFIKITVVWLISIGIAIPVPIKGIETDVD

NPNNITCVLTKERFGDFMLFGSLAAFFTPLAIMIVTYFLTIHALQKKAYL

VKNKPPQRLTWLTVSTVFQRDETPCSSPEKVAMLDGSRKDKALPNSGDET

LMRRTSTIGKKSVQTISNEQRASKVLGIVFFLFLLMWCPFFITNITLVLC

DSCNQTTLQMLLEIFVWIGYVSSGVNPLVYTLFNKTFRDAFGRYITCNYR

ATKSVKTLRKRSSKIYFRNPMAENSKFFKKHGIRNGINPAMYQSPMRLRS

STIQSSSIILLDTLLLTENEGDKTEEQVSYV

In some embodiments, the serotonin receptor comprises SEQ ID NO: 2 (amino acids 1-471 having GenBank Accession No. NP_000612.1):

MDILCEENTSLSSTTNSLMQLNDDTRLYSNDFNSGEANTSDAFNWTVDSE

NRTNLSCEGCLSPSCLSLLHLQEKNWSALLTAVVIILTIAGNILVIMAVS

LEKKLQNATNYFLMSLAIADMLLGFLVMPVSMLTILYGYRWPLPSKLCAV

WIYLDVLFSTASIMHLCAISLDRYVAIQNPIHHSRFNSRTKAFLKIIAVW

TISVGISMPIPVFGLQDDSKVFKEGSCLLADDNFVLIGSFVSFFIPLTIM

VITYFLTIKSLQKEATLCVSDLGTRAKLASFSFLPQSSLSSEKLFQRSIH

REPGSYTGRRTMQSISNEQKACKVLGIVFFLFVVMWCPFFITNIMAVICK

ESCNEDVIGALLNVFVWIGYLSSAVNPLVYTLFNKTYRSAFSRYIQCQYK

ENKKPLQLILVNTIPALAYKSSQLQMGQKKNSKQDAKTTDNDCSMVALGK

QHSEEASKDNSDGVNEKVSCV

In some embodiments, the serotonin receptor comprises SEQ ID NO: 3 (amino acids 1-458 having GenBank Accession No. NP_000859.1):

MVNLRNAVHSFLVHLIGLLVWQCDISVSPVAAIVTDIFNTSDGGRFKFPD

GVQNWPALSIVIIIMTIGGNILVIMAVSMEKKLHNATNYFLMSLAIADM

LVGLLVMPLSLLAILYDYVWPLPRYLCPVWISLDVLFSTASIMHLCAISL

DRYVAIRNPIEHSRFNSRTKAIMKIAIVWAISIGVSVPIPVIGLRDEEKV

FVNNTTCVLNDPNFVLIGSFVAFFIPLTIMVITYCLTIYVLRRQALMLLH

GHTEEPPGLSLDFLKCCKRNTAEEENSANPNQDQNARRRKKKERRPRGTM

QAINNERKASKVLGIVFFVFLIMWCPFFITNILSVLCEKSCNQKLMEKLL

NVFVWIGYVCSGINPLVYTLFNKIYRRAFSNYLRCNYKVEKKPPVRQIPR

VAATALSGRELNVNIYRHTNEPVIEKASDNEPGIEMQVENLELPVNPSSV

VSERISSV

In some embodiments, the compound of the invention can bind to amino acid residue(s) of a serotonin receptor comprising position(s) 113, 114, 118, 131, 132, 133, 135, 136, 139, 140, 190, 203, 207, 209, 213, 214, 217, 218, 221, 222, 225, 242, 293, 308, 336, 337, 339, 340, 341, 343, 344, 362, 363, 366, 367, or a combination thereof, of SEQ ID NOS: 1, 2, or 3.

In some embodiments, the compound of the invention can bind to amino acid residues T114, W131, L132, D135, V136, S139, T140, V190, L209, F214, F217, M218, G221, S222, A225, H242, W337, F340, F341, N344, L362, E363, V366, or a combination thereof, of SEQ ID NO: 1.

In some embodiments, the compound of the invention can bind to amino acid residues M114, S131, L133, I135, L136, Y139, R140, T190, S203, S207, P209, F213, D217, D218, V221, F222, G225, S242, W336, F339, F340, N343, L362, N363, V366, or a combination thereof, of SEQ ID NO: 2.

Embodiments as described herein can be administered to a subject as a prodrug. A prodrug is a medication or compound that, after administration, is metabolized into a pharmaceutically active drug. Inactive prodrugs are pharmacologically inactive medications or compounds that are metabolized into an active form within the body.

Specific 5-HT$_{2A}$ agonists used in the present invention can be administered to a patient by any suitable means, including ocular (e.g., topical ocular (e.g., by eye drop of gel) or intra-ocular), oral, intravenous, parenteral, subcutaneous, intrapulmonary, topical, intravitreal, dermal, transmucosal, rectal, and intranasal administration. Ocular administration includes eye drop administration, topical gel administration, instillation in the conjunctival sac, intravitreal administration, subconjunctival administration or sub-Tenon's administration. Parenteral infusions include intramuscular, intravenous, intraarterial, or intraperitoneal administration. The compounds can also be administered transdermally, for example in the form of a slow-release subcutaneous implant or as a transdermal patch. They can also be administered by inhalation. Although direct oral administration can cause some loss of anti-inflammatory activity, the agonists can be packaged in such a way to protect the active ingredient(s) from digestion by use of enteric coatings, capsules or other methods known in the art.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

The compound of formula (I), (II), or (III), or the composition comprising a compound of formula (I), (II), or (III) can be administered to the subject one time (e.g., as a single injection or deposition). Alternatively, administration can be once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12, 13, 14, 15, 16, 17, 18, 19, 20, 21, 22, 23, 24 times per year, or a combination thereof.

The dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

In some embodiments, the therapeutically effective amount of a compound of the invention (e.g., the serotonin receptor agonist and/or additional therapeutic agent) administered to a subject is at least about 0.0001 mg/kg body weight, 0.0005 mg/kg body weight, 0.001 mg/kg body weight, 0.005 mg/kg body weight, 0.01 mg/kg body weight, 0.05 mg/kg body weight, 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

In some embodiments, the therapeutically effective amount of a compound of the invention (e.g., the serotonin receptor agonist and/or additional therapeutic agent) administered to a subject is from 0.0001 mg/kg body weight to 0.0005 mg/kg body weight, from 0.0005 mg/kg body weight to 0.001 mg/kg body weight, from 0.001 mg/kg body weight to 0.005 mg/kg body weight, from 0.01 mg/kg body weight to 0.05 mg/kg body weight, from 0.05 mg/kg body weight to 0.1 mg/kg body weight, from 0.1 mg/kg body weight to 0.5 mg/kg body weight, from 0.5 mg/kg body weight to 1.0 mg/kg body weight, from 1.0 mg/kg body weight to 2.0 mg/kg body weight, from 2.0 mg/kg body weight to 3.0 mg/kg body weight, from 3.0 mg/kg body weight to 4.0 mg/kg body weight, from 4.0 mg/kg body weight to 5.0 mg/kg body weight, from 5.0 mg/kg body weight to 7.5 mg/kg body weight, from 7.5 mg/kg body weight to 10 mg/kg body weight, from 10 mg/kg body weight to 25 mg/kg body weight, from 25 mg/kg body weight to 50 mg/kg body weight, from 50 mg/kg body weight to 100 mg/kg body weight, from 100 mg/kg body weight to 250 mg/kg body weight, from 250 mg/kg body weight to 500 mg/kg body weight, or from 500 mg/kg body weight to 100 mg/kg body weight.

In some embodiments, the serotonin receptor agonist is administered to a subject in a low dose (e.g., a sub-perceptive dose, e.g., such that the subject's behavior is not altered). For example, a sub-perceptive dose can be less than about 100 µg/kg, less than about 75 µg/kg, less than about 50 µg/kg, less than about 25 µg/kg, less than about 10 µg/kg, less than about 7.5 µg/kg, less than about 5.0 µg/kg, less than about 2.0 µg/kg, less than about 1.5 µg/kg, less than about 1.0 µg/kg, less than about 0.5 µg/kg, less than about 0.1 µg/kg, or lower.

Any of the therapeutic applications described herein can be applied to any subject in need of such therapy, including, for example, a mammal such as a human, mouse, a rat, a dog, a cat, a cow, a horse, a rabbit, a monkey, a pig, a sheep, or a goat. In some embodiments, the subject is a mouse, rat, pig, or human. In some embodiments, the subject is a mouse. In some embodiments, the subject is a rat. In some embodiments, the subject is a pig. In some embodiments, the subject is a human.

In some embodiments, the therapeutic applications described herein can be applied in a veterinary setting. For example, the subject may be a cat or a dog.

Compounds of formula (I), (II), or (III) can be incorporated into pharmaceutical compositions suitable for administration. Such compositions can comprise a compound of formula (I), (II), or (III) and a pharmaceutically acceptable carrier. Thus, in some embodiments, the compounds of the invention are present in a pharmaceutical composition.

In embodiments, the agonist is DOI. In other embodiments, the agonist is not DOI.

Compositions

The term "composition" can refer to a single compound, or can refer to a combination of at least two compounds. For example, a composition can comprise a serotonin receptor agonist and a pharmaceutically acceptable carrier. In other embodiments, the composition can comprise more than two compounds. For example, a composition can comprise a serotonin receptor agonist (e.g., a 5-HT$_{2A}$ receptor agonist, e.g., DOI), an antipathogenic agent (e.g., an antiviral agent, e.g., TFT or ganciclovir), and a pharmaceutically acceptable carrier.

Pharmaceutically acceptable carrier preparations include sterile, aqueous or non-aqueous solutions, suspensions, and emulsions. Examples of non-aqueous solvents are propylene glycol, polyethylene glycol, carboymethylcellulose, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers dextrose, dextrose and sodium chloride, lactated Ringers, or fixed oils. The active therapeutic ingredient can be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, inert gases, and the like.

Embodiments, such as those suitable for ocular uses, incorporate additives to increase dispersion of the drugs in the eye while also increasing retention in the eye. Nonlimiting examples of such additives comprise carboxymethylcellulose or polyethylene glycol.

Ophthalmic formulations of the invention include topical formulations, such as eye drops, gels, and ointments. Ophthalmic solutions may contain one or more viscosity-adjusting agent and have a viscosity of 1.0 to 100,000 cP (e.g., from 2.0 to 90,000 cP or from 2.5 and 75,000 cP), which is acceptable since compositions in this range of viscosity feel comfortable to the eye and do not cause blurring of the vision. Viscosity modifying agents can be used in ophthalmic compositions and are substances that have the ability to cause thickening (increase the viscosity) of ophthalmic formulations. Viscosified solutions are accepted to a great degree by patients, mainly because of the ease of administration. Viscosity modifying agents include xanthan gum, edetate, methylcellulose, carboxymethylcellulose, hydroxypropyl methylcellulose, hydroxyethyl cellulose, polyethylene glycol, propylene glycol alginate, chitosan, and tragacanth. Hydrogels are often used as viscosity enhancing excipients, particularly in artificial tears and refers to a colloid with high gelling ability. If needed, compatible viscosity-adjusting agents can be used in all formulations mentioned herein. When needed, the concentrations of the selected viscosity modifying agents range from about 0.1 percent to about 10 percent by weight, and preferably between 1 percent and 5 percent. Sorbitol may be used as a combined tonicity-adjusting and viscosity-adjusting excipient in a concentration range from about 0.1 to about 10 percent, preferably from 2 percent to 5 percent.

The form can vary depending upon the route of administration. For example, compositions for injection can be provided in the form of an ampoule, each containing a unit dose amount, or in the form of a container containing multiple doses. In some embodiments, parenteral preparations can be enclosed in ampoules, disposable syringes or multiple dose vials made of glass or plastic.

In some embodiments, pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

In some embodiments, sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

In some embodiments, oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

A compound in accordance with the present invention can be formulated into therapeutic compositions as pharmaceutically acceptable salts, for example a hydrochloride salt (e.g., the (R)-DOI used in the above examples). These salts include acid addition salts formed with inorganic acids, for example hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

A method for controlling the duration of action comprises incorporating the active compound into particles of a polymeric substance such as a polyester, peptide, hydrogel, polylactide/glycolide copolymer, or ethylenevinylacetate copolymers. Alternatively, an active compound can be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In embodiments, the serotonin receptor agonist can be administered to a subject in a composition comprising at least one additional bioactive agent. Non-limiting examples of bioactive agents comprise an antimicrobial agent, an anti-pathogenic agent, a drug, or a combination thereof. Non-limiting examples of antimicrobial agents comprise an antiviral agent, an antibacterial agent, an antibiotic agent, an antifungal agent, an antiprotozoal agent, or a combination thereof.

Any suitable anti-infective agent(s) (e.g., anti-biotic agents, e.g., antiviral agents or antibacterial agents) may be administered in combination with (e.g., at the same time or a different time) a serotonin receptor agonist. Anti-infective agents and formulations suitable for ophthalmic administration include, for example, levofloxacin, natamycin, tobramycin, polymyxin b/trimethoprim, ciprofloxacin, trifluridine, moxifloxacin, gatifloxacin, besifloxacin, moxifloxacin, ganciclovir, azithromycin, chloramphenicol, bacitracin/polymyxin b, tobramycin, povidone iodine, sulfacetamide sodium, idoxuridine, erythromycin, gentamicin, bacitracin/neomycin/polymyxin b, gramicidin/neomycin/polymyxin b, ofloxacin, oxytetracycline/polymyxin b, tobramycin, vidarabine, and gatifloxacin.

In embodiments, non-limiting examples of an antiviral agent useful as part of the invention include TFT, acyclovir, ganciclovir, penciclovir, famiciclovir, cidofovir and its analog derivatives; ribavirin, interferon, phosphonoacetate, foscarnet, and valaciclovir. TFT and ganciclovir, for example, are relevant for the infections of the eye, such as in herpetic infections.

Kits

The invention further provides kits that can have one or more containers (e.g., bottles, blister packs, vials, ampoules) containing unit dosage forms comprising the compositions described above, and, optionally, one or more additional pharmaceutical agents. Each agent (e.g., the serotonin receptor agonist or the antiviral agent) can be contained in separate containers or in the same container. Associated with such container(s) (e.g., enclosed in a package together with the container) can be a notice in the form prescribed by a governmental agency regulating the manufacture, use or sale of pharmaceutical products (e.g., the US Food & Drug Administration or European Medicines Agency), which reflects approval by the agency of manufacture of use or sale for human administration for treatment of acute or chronic pain. The notice can describe, e.g., doses, routes and/or methods of administration, approved indications, methods of monitoring for therapeutically effective levels, and/or other information of use to a medical practitioner and/or patient.

EXAMPLES

Physiological angiogenesis and neovascularization are required for embryonic development, tissue remodeling, and wound healing. However, in certain tissues and diseases, dysregulation of these tightly controlled processes can result in vascularization-mediated pathological conditions. Pathological vascularization and dysregulation of vascular function are critical determinates in the outcomes of ocular neovascularization diseases, including stromal keratitis, proliferative retinopathies, and macular degeneration. The following examples demonstrate that activation of the 5-$HT_{2A}$ receptor by agonistic agents (e.g., DOI) effectively suppresses vascularization-associated processes.

The following examples are provided below to facilitate a more complete understanding of the invention and illustrate exemplary modes of making and practicing the invention. However, the scope of the invention is not limited to specific embodiments disclosed in these examples, which are for purposes of illustration only. It will be understood by a person of skill in the art that variations of these methods can be utilized to obtain similar results.

Example 1. Treatment of Herpes Keratitis

Serotonin or 5-hydroxytryptamine (5-HT) is a small monoamine molecule primarily known for its role as a neurotransmitter. Within the brain, 5-HT modulates a variety of behaviors including cognition, mood, aggression, mating, feeding, and sleep (Nichols and Nichols, 2008). These behaviors are mediated through interactions at seven different receptor families (5-$HT_{1-7}$) comprised of fourteen distinct subtypes (Nichols and Nichols, 2008). Each of these are G-protein coupled receptors, with the exception of the 5-$HT_3$ receptor, which is a ligand-gated ion channel. Of all the serotonin receptors, the 5-$HT_{2A}$ receptor, which is known to primarily couple to the Gaq effector pathway (Roth et al., 1986), has been the one most closely linked to complex behaviors.

Figure 2:
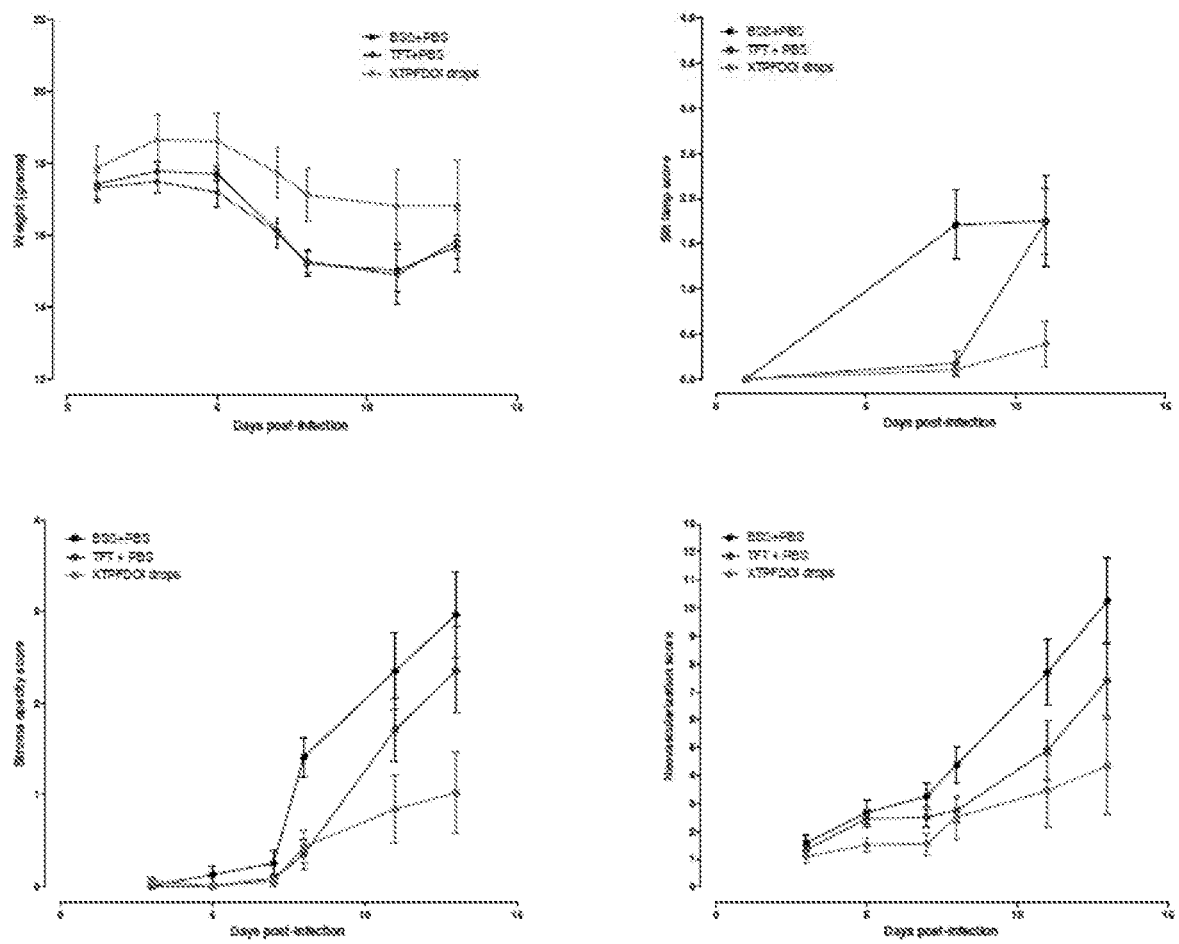
FIG. 2 shows comparison of Acute and Chronic Disease Scores in BALBc mice following treatment with BSS, 1% TFT, and XTPFDOI; Treatment: 4 µl/eye/4× daily for 8 days (treatment duration did not exceed 8 days); Infection model Herpes Stromal Keratitis; BALBc; HSV-1 RE; 10,000 PFU/eye; Clinical Assessment Parameters Shown: Weight; Slit-Lamp Biomicroscopy of Eye; Stromal Opacity/Inflammation; Corneal Neovascularization.
Figure 4:
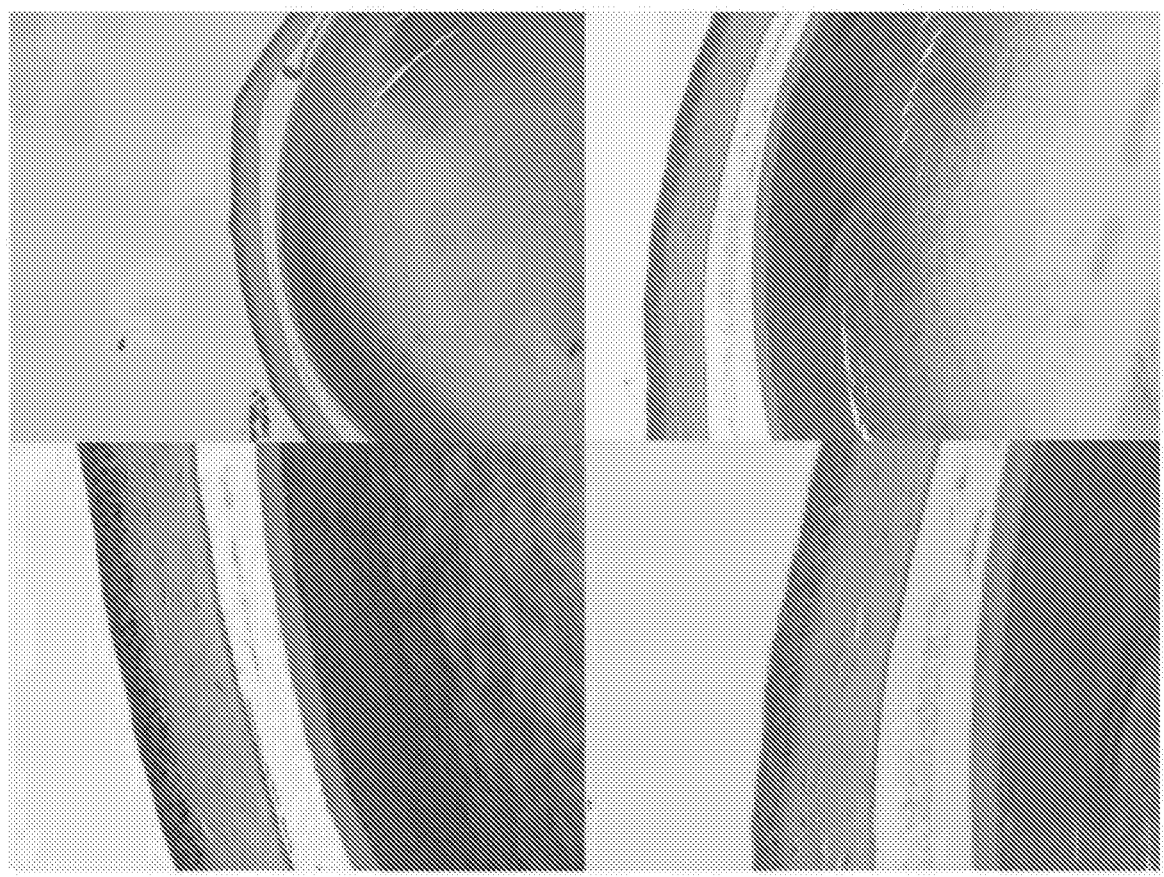
FIG. 4 shows ocular histology of eyes from BalBc experiments examining ability of DOI to control long-term chronic effects of HSV-mediated stromal keratitis: DAY 15 post infection. Uninfected normal eyes.
Figure 5A:
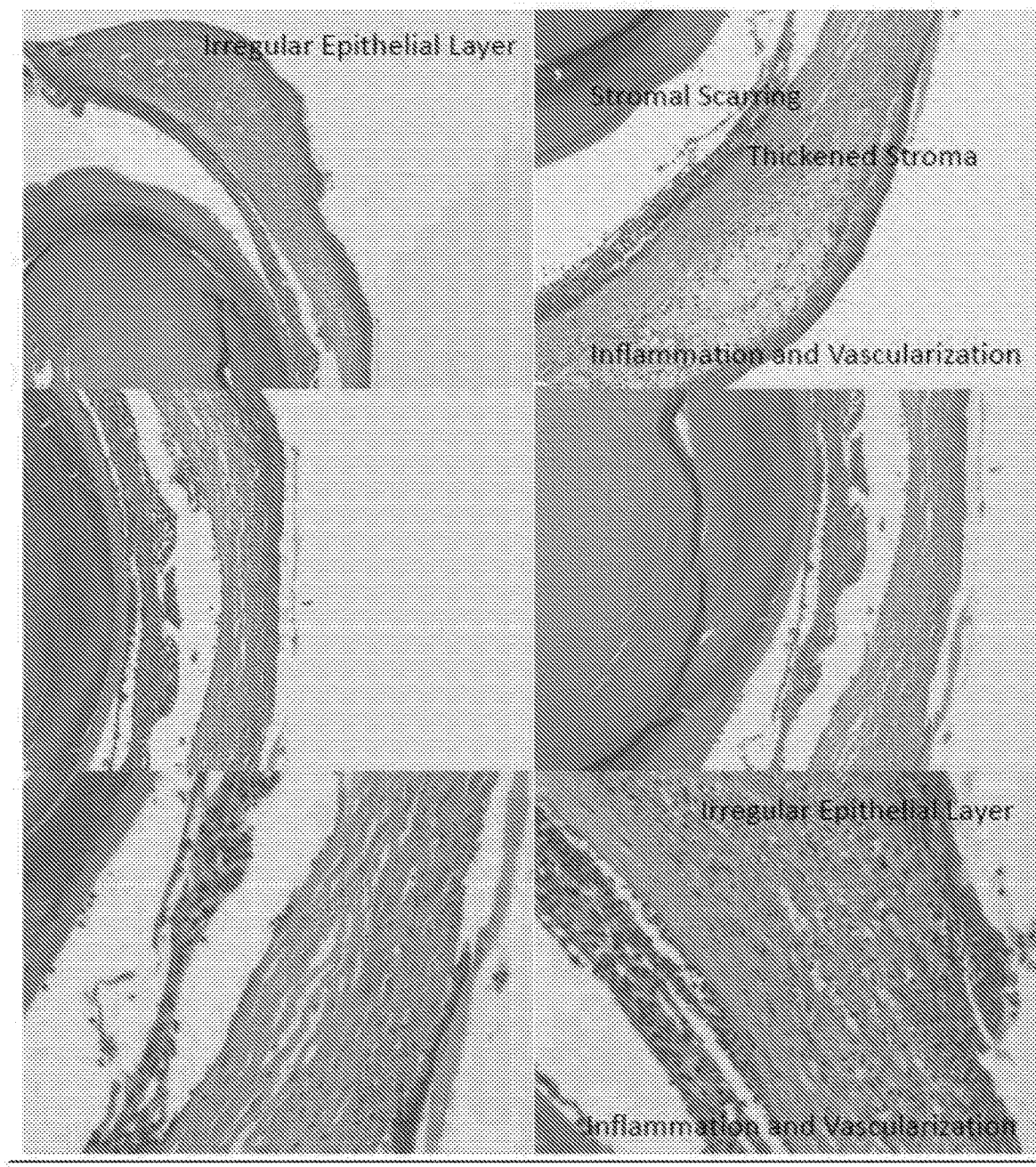
FIG. 5A shows eye 1.
Figure 5B:
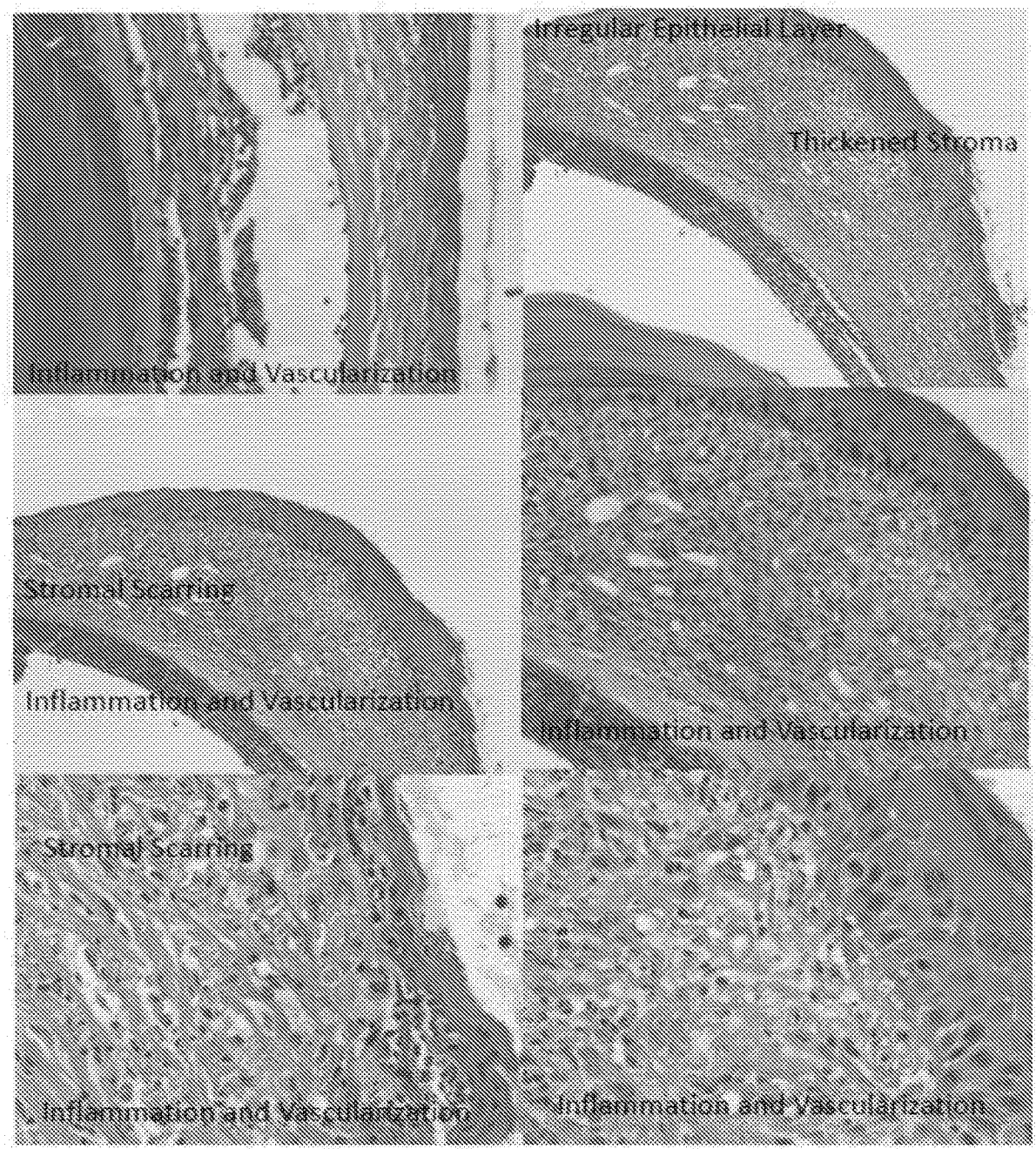
FIG. 5B shows eye 2.
Figure 5C:
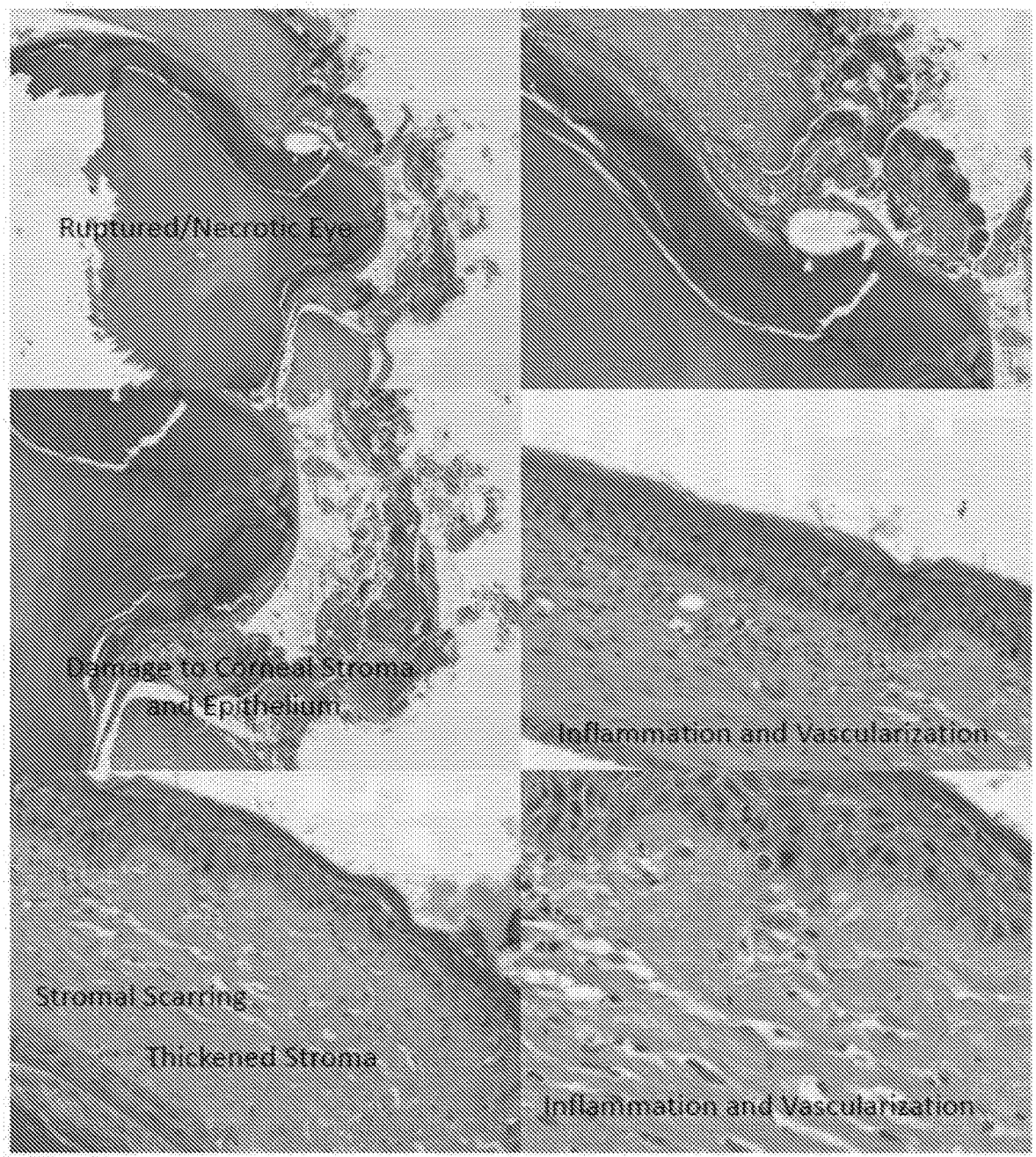
FIG. 5C shows eye 3.
Figure 6A:
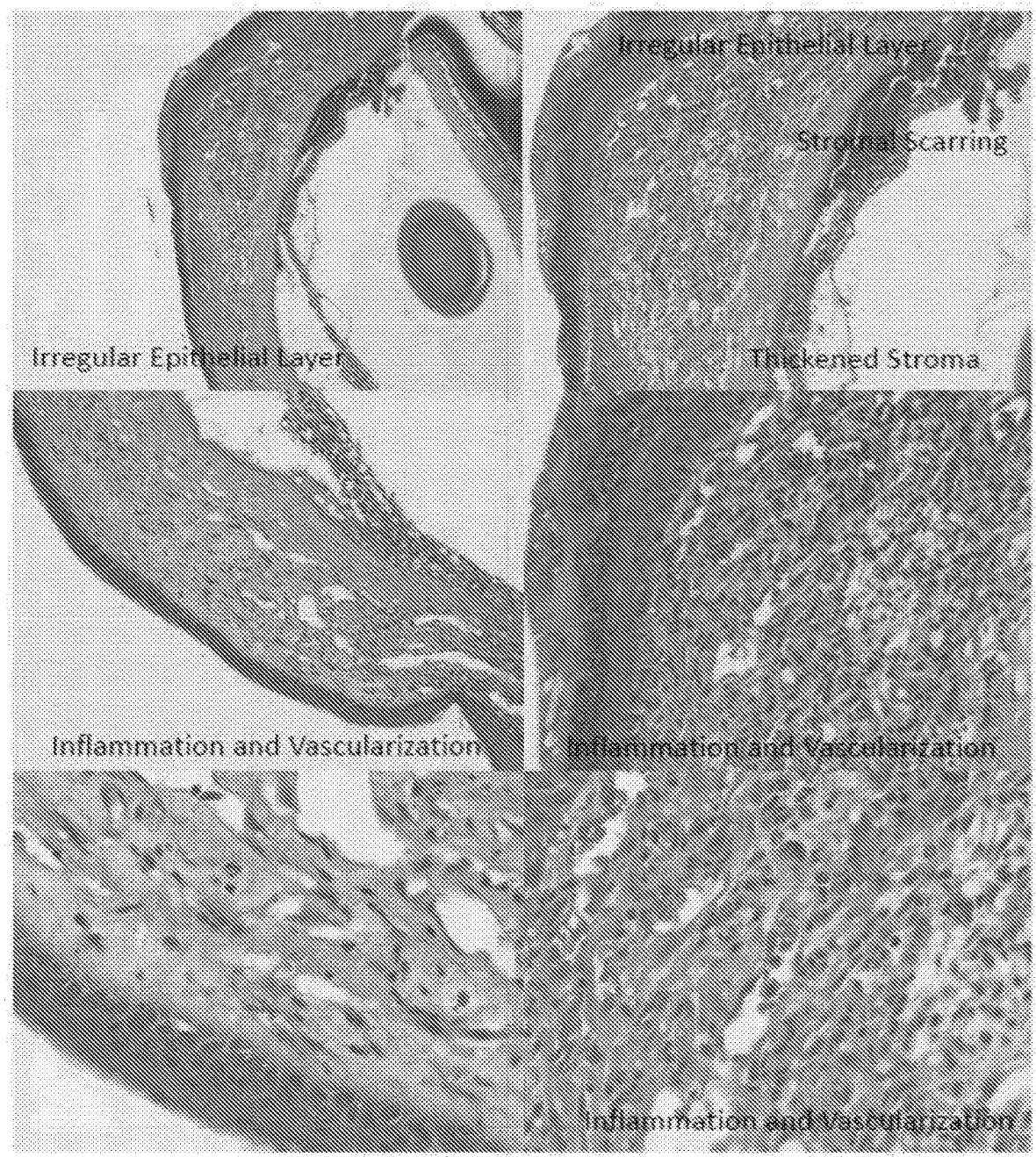
FIG. 6A shows eye 1.
Figure 6B:
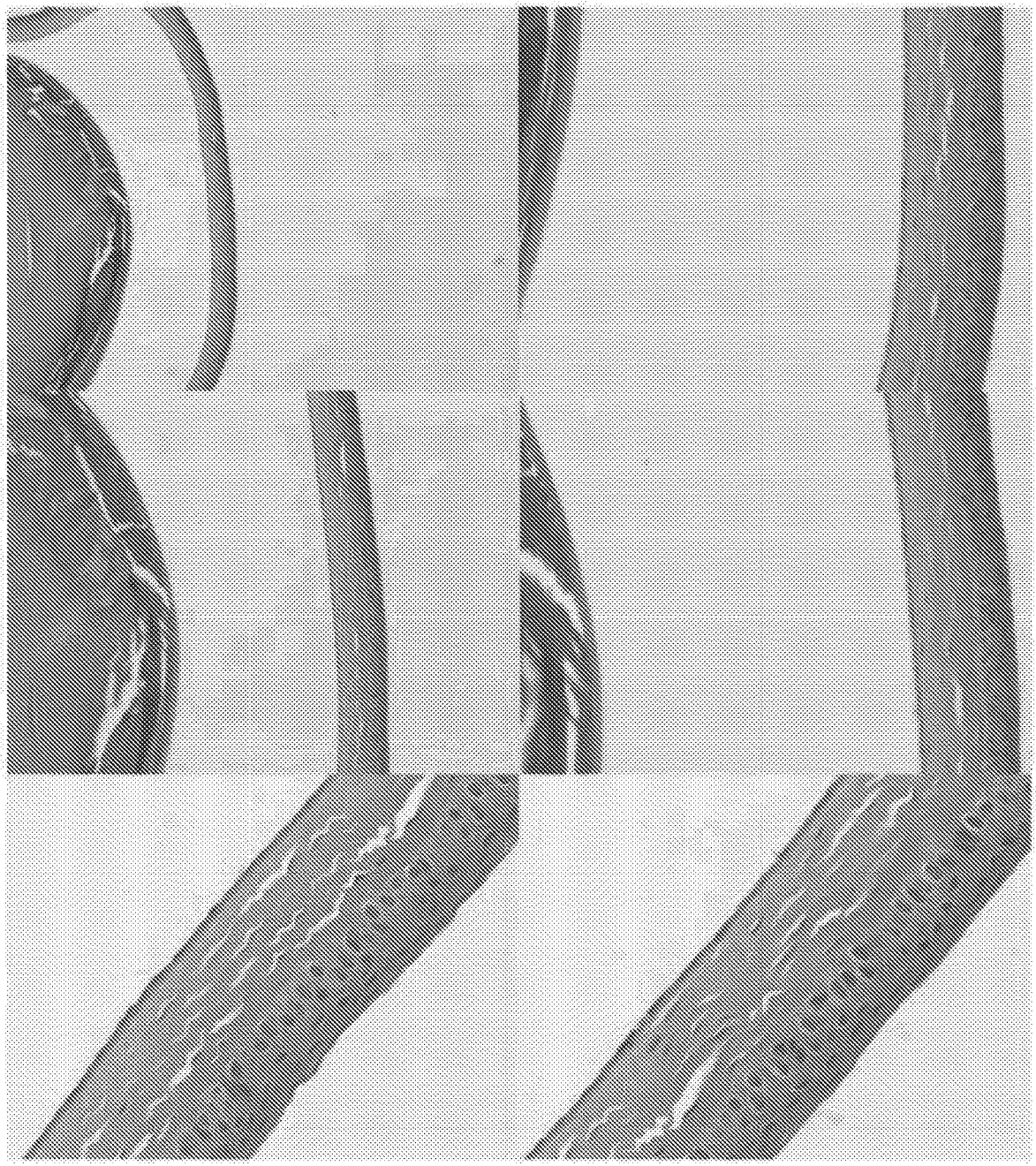
FIG. 6B shows eye 1.
Figure 6C:
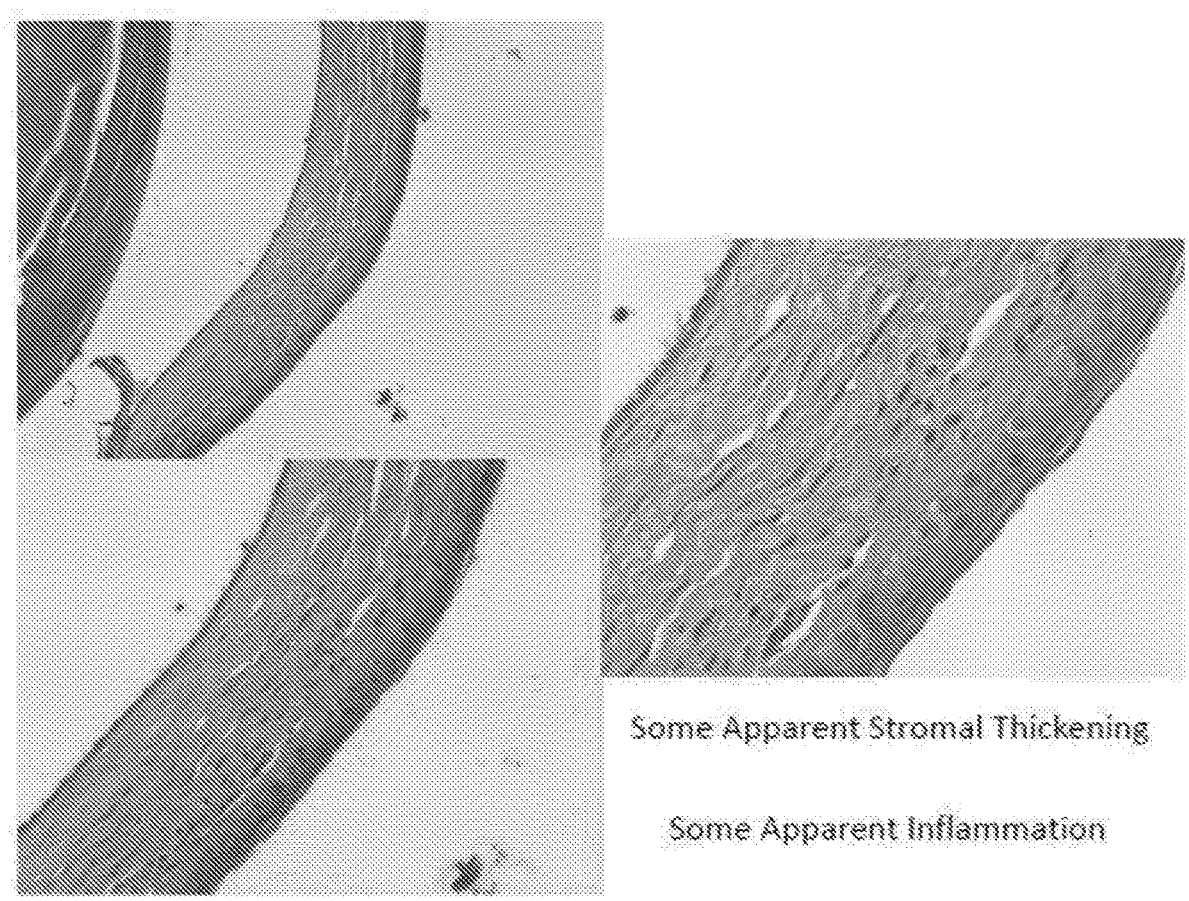
FIG. 6C shows eye 2 (worse of the Tx group).

Agonists of the serotonin receptor pathway, such as DOI, can be delivered systemically or topically (e.g., through a topical ocular drop) to prevent and resolve pathogen-elected host-mediated disease processes. Such a topical formulation may involve inclusion of secondary compounds that prevent viral replicative processes. We have compared different topical ocular compositions and demonstrated that, in a herpetic disease model, inclusion of DOI effectively suppressed acute and chronic herpes-associated eye disease. Importantly, in a herpetic eye disease model, DOI was superior at controlling both acute and chronic vision-threatening disease when compared to the gold-standard anti-herpetic, trifluorothymidine (TFT). Specifically, treatment with compositions that included DOI suppressed disease processes including neovascularization of the cornea, trafficking of immune cells into the cornea, and epithelial and stromal damage. DOI was been tested with and without inclusion of additional compounds (e.g., compounds that suppress pathogen replicative processes, e.g., TFT; FIGS. 1 and 2). Despite the availability of effective anti-infectives that can suppress replication of specific pathogens, pathogen-mediated processes cause severe disease presentation that can become a chronic self-perpetuating process. In the eye, accumulation of disease-mediated processes can result in severe disease presentations that are independent of the replication of the pathogen. Therefore, effective treatment and resolution of the pathogen by current anti-infectives often cannot in of itself prevent chronic disease processes that ultimately damages (e.g., scars) ocular tissues. This includes pathological vascularization of the tissue. Treatment with serotonin-agonists, such as DOI, is a new approach that can suppress these host mediated disease processes without some of the potential side effects that are associated with classical treatments (e.g., immunosuppressive treatments). Our data indicates that compounds such as DOI can effectively prevent acute and chronic herpetic eye disease that normally results in severe irreversible destruction of the cornea and scarring. DOI also prevented pathological vascularization of the normally avascular cornea, a process that contributes to several eye-associated disease processes. Drugs that prevent pathogen replication fail to control these processes and, as such, the disease progresses irrespective of a drug's ability to control pathogen replication. Therefore, use of serotonin receptor agonists alone, or in combination with other antiinfectives (e.g., antiviral agents), appears to be an effective means in preventing long-term chronic consequences of herpetic infection and associated acute and chronic disease processes.

C57bl/6 mice were randomly sorted into 3 treatment arms: 1) Ophthalmic Balanced Saline Solution (BSS) treated; 2) DOI treated (XTPFDOI); 3) 0.5% TFT with DOI (TFT+XTPFDOI). Animals were anesthetized with xylene:ketamine and both eyes were scarified in a cross hatch pattern using a curved needle. Immediately following ocular scarification, eyes were inoculated with a 3 microliter drop containing 12,000 plaque forming units (PFU) of Herpes Simplex Virus type 1 (HSV-1) RE strain. The next morning following infection animals were treated with the respective treatment as assigned within their treatment arm. Treatments were applied topically to the eye in a 4 microliter drop. Drops were applied 4 times per day from 9:00 am to 5:30 pm, starting immediately following clinical scoring. Treatments were applied for the first 8 days post infection and then stopped. Clinical scoring was done using a slit lamp biomicroscope magnified at 16× on the days indicated by a single individual masked to the drug treatment parameters. Slit lamp biomicroscopy also included fluorescein exclusion labeling of the corneal surface following scoring of all clinical parameters. Each eye was scored independently.

Results of the C57bl/6 mouse model studies are shown in FIG. 1. Relative to BSS controls, mice treated with DOI had a decreased score in all three metrics tested by day 12 post-infection. By day 16 post-infection, DOI-treated mice showed an even greater improvement in each metric compared to the BSS control. Combination of TFT with DOI improved this effect in each of the three metrics tested.

16 BALB/c mice were randomly sorted into 3 treatment arms: 1) Ophthalmic Balanced Saline Solution diluted 1:1 in PBS (BSS+PBS) treated (6 mice); 2) DOI treated (XTPF-DOI) (5 mice); 3) 1.0% TFT (TFT+PBS) (5 mice). Animals were anesthetized with xylene:ketamine and both eyes were scarified in a cross hatch pattern using a curved needle. Immediately following ocular scarification, eyes were inoculated with a 3 microliter drop containing 10,000 plaque forming units (PFU) of Herpes Simplex Virus type 1 (HSV-1) RE strain. The next morning following infection, animals were treated with the respective treatment as assigned within their treatment arm. Treatments were applied topically to the eye in a 4 microliter drop. Drops were applied 4 time per day from 9:00 am to 5:30 pm, starting immediately following clinical scoring. Treatments were applied for the first 8 days post infection and then stopped. Clinical scoring was done using a slit lamp biomicroscope magnified at 16× on the days indicated by a single individual masked to the drug treatment parameters. Slit lamp biomicroscopy also included fluorescein exclusion labeling of the corneal surface following scoring of all clinical parameters. Each eye was scored independently. Animal deaths were recorded if euthanasia was required due to severe encephalitis or if animals died from HSV-associated disease. Clinically clear eyes were scored as such if no apparent signs of disease were present in any clinical parameter during the chronic phase.

Results of the BALB/c mouse model study are shown in FIG. 2. Relative to BSS controls and TFT controls, mice treated with DOI had a decreased slit lamp score, stroma capacity score, and neovascularization score in all three metrics tested by day 12 post-infection. Further, animal body weight was retained in DOI-treated mice, whereas TFT treatment did not change body weight relative to BSS controls.

At day 15 post infection, a stage that would be during chronic immune-associated disease with no virus present, animals were euthanized and the eyes were removed for histology. Random representative eyes were prepared by taking sections through the central cornea and processed by H&E histology for visualization. Sections were examined microscopically and photographed across the central cornea. Multiple eyes from each group that showed the best representation of that groups clinical scores extremes and midpoints are shown in FIGS. 3-9.

Example 2: Development of Preclinical Models

The data presented above shows that DOI potently inhibited disease-associated vascularization of the eye, preventing the chronic pathology normally associated with disease progression. Without wishing to be bound by theory, DOI may modulate vasculogenesis and vascular homeostasis in these disease processes through direct or indirect effects on vascular cells.

To evaluate the effects of DOI on pathological vascularization-associated ocular herpetic stromal keratitis, additional animal model systems may be developed as described herein. The model system can be complemented by established in vitro mechanistic studies to assess the direct effects of DOI on vascular cell biology and function. The contributions of 5-HT receptors in this disease process can likewise be explored.

Evaluation of Therapeutic Efficacy of 5-HT Receptor Modulation for Amelioration of Pathological Vascularization-Associated Conditions Data demonstrates that the 5-HT agonist, R-DOI, can suppress disease processes within the eye. Specifically, ophthalmic formulations of R-DOI suppressed HSV-induced pathological vascularization of the eye and abolished chronic host-mediated vision-threatening disease processes. Without wishing to be bound by theory, this indicates that 5-HT receptors participate in the associated disease processes within ocular tissues and that modulation of specific 5-HT receptor activities has therapeutic potential for prevention and resolution of ocular disease.

Therapeutic efficacy is assessed by: 1) clinical scoring as outlined in disease specific models; 2) histopathological findings; 3) supportive immunological data, including sera inflammatory cytokine levels and infiltration of cells within effected tissues.

Figure 7:
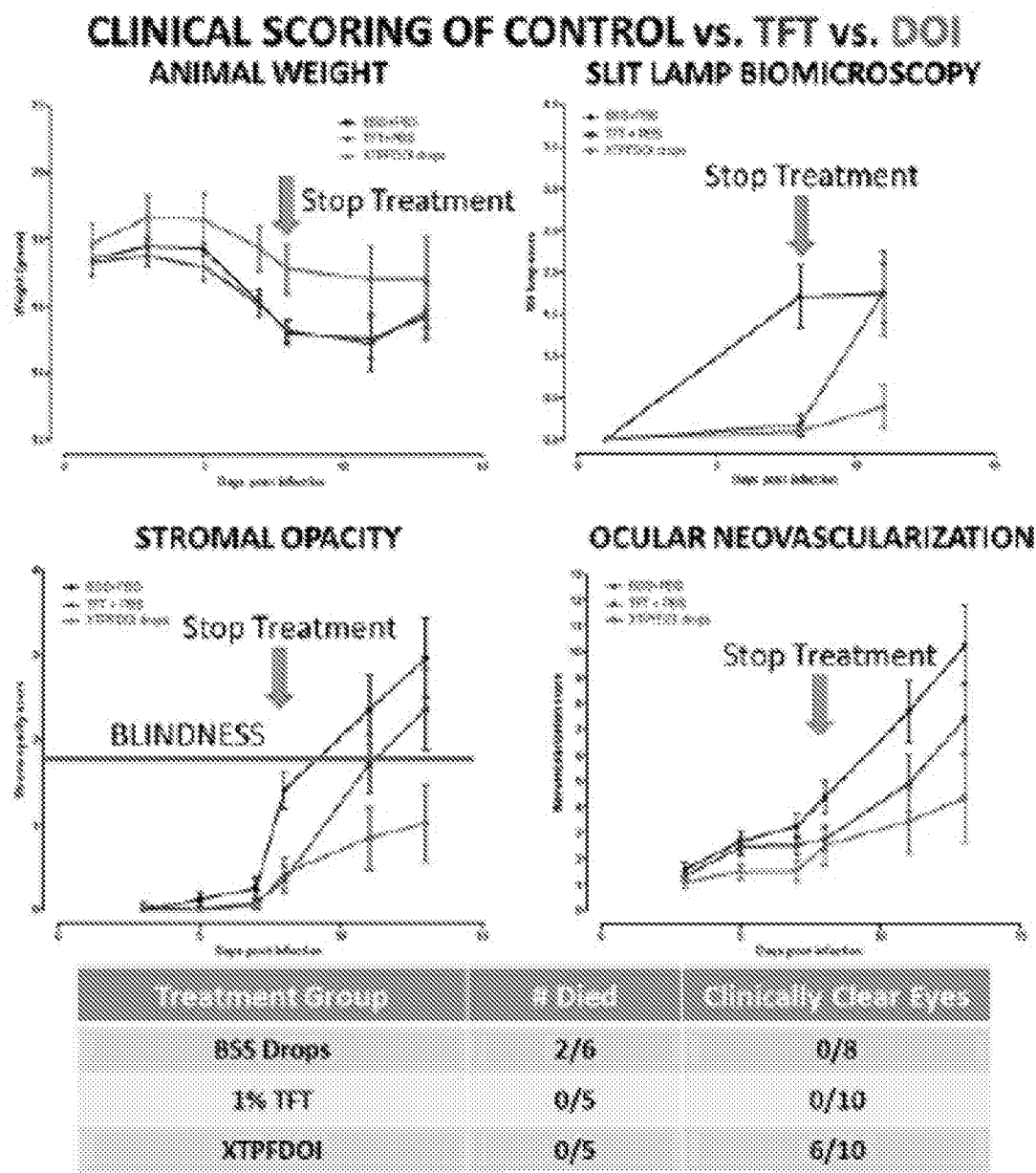
FIG. 7 shows a comparative preclinical assessment of therapeutic efficacy of a 5-HT receptor agonist (XTPFDOI, red), compared to the gold standard ocular antiviral 1% TFT/Viroptic (blue) or control saline drops (black) in a herpetic stromal keratitis ocular chronic disease model. DOI drops were topically applied for 7 days post infection and chronic disease was assessed up to day 15. DOI suppressed development of all clinically scored parameters with 60% of eyes exhibiting complete clinical resolution by day 15.
Figure 8:
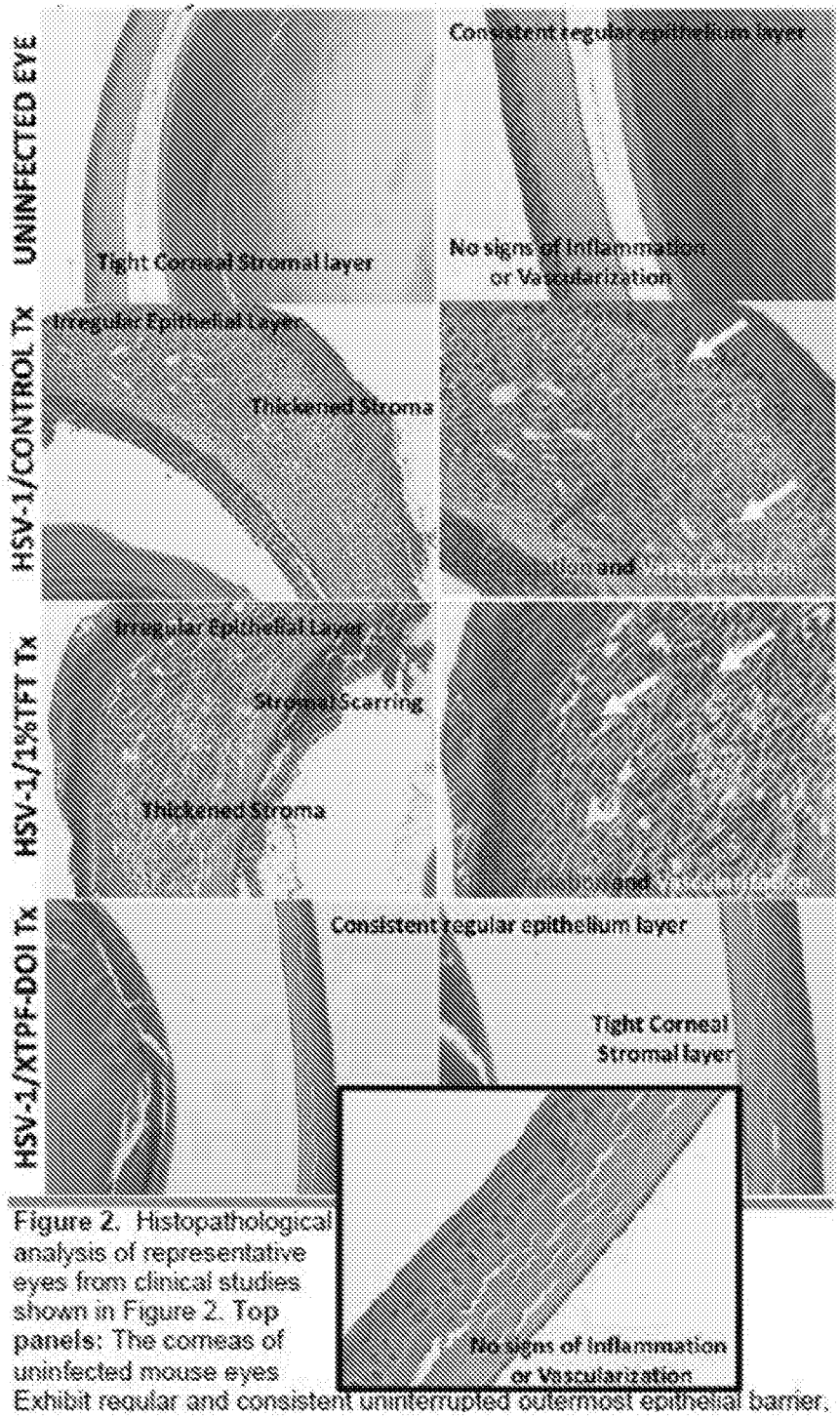
FIG. 8 shows histopathological analysis of representative eyes from clinical studies shown in FIG. 2. Top panels: The corneas of uninfected mouse eyes exhibit regular and consistent uninterrupted outermost epithelial barrier, and an underlying tight corneal stromal layer of even thickness. There is a complete absence of inflammatory or red blood cells and no vascularization of corneal tissue. 2nd row panels: HSV infection and long-term inflammatory responses induces disruption of the epithelial layer, thickening of the stroma, and identifiable vascularization of corneal tissue (yellow arrows) with extensive presence of immune infiltrates. 3rd row panels: Despite treatment with the antiviral TFT and complete inhibition of HSV replication, similar disease processes to control Tx predominate at 15 days. 4th row panels and enlarged inset: By contrast, eyes treated with the 5-HT agonist DOI have normal ocular morphology with an absence of clinical signs of ocular disease.
Figure 9:
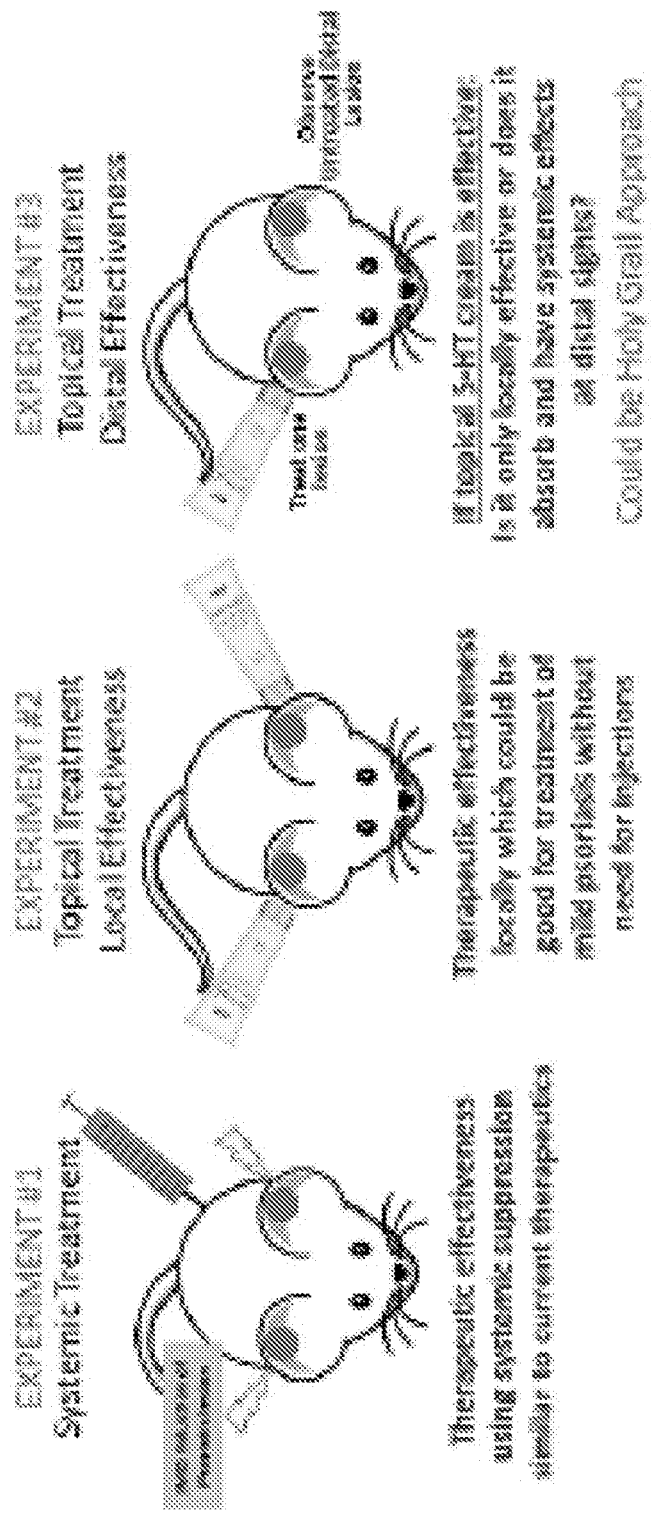
FIG. 9 shows a series of experiments to assess the effect of systemic and topical treatment.

An ophthalmic topical formulation of DOI (here, XTPF-DOI) was developed and its ability to inhibit the long-term vascularization-mediated disease processes that are responsible for inducing corneal blindness following HSV infection was assessed. Data from a mouse model of herpetic stromal keratitis (HSK) demonstrated that DOI was effective at suppressing HSV-associated ocular disease sequelae and progression to blindness (FIGS. 7 and 8).

Rabbit Model of Herpetic Stromal Keratitis

Figure 10:
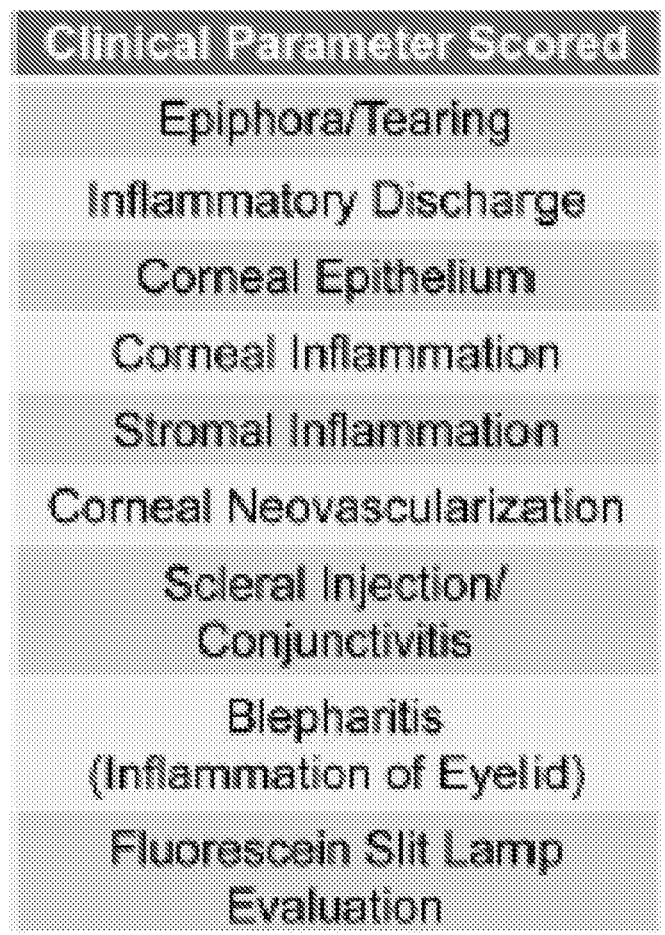
FIG. 10 is a table listing various parameters that are scored clinically to quantitatively characterize response to conditions associated with pathological neovascularization or herpes keratitis.
Figure 11:
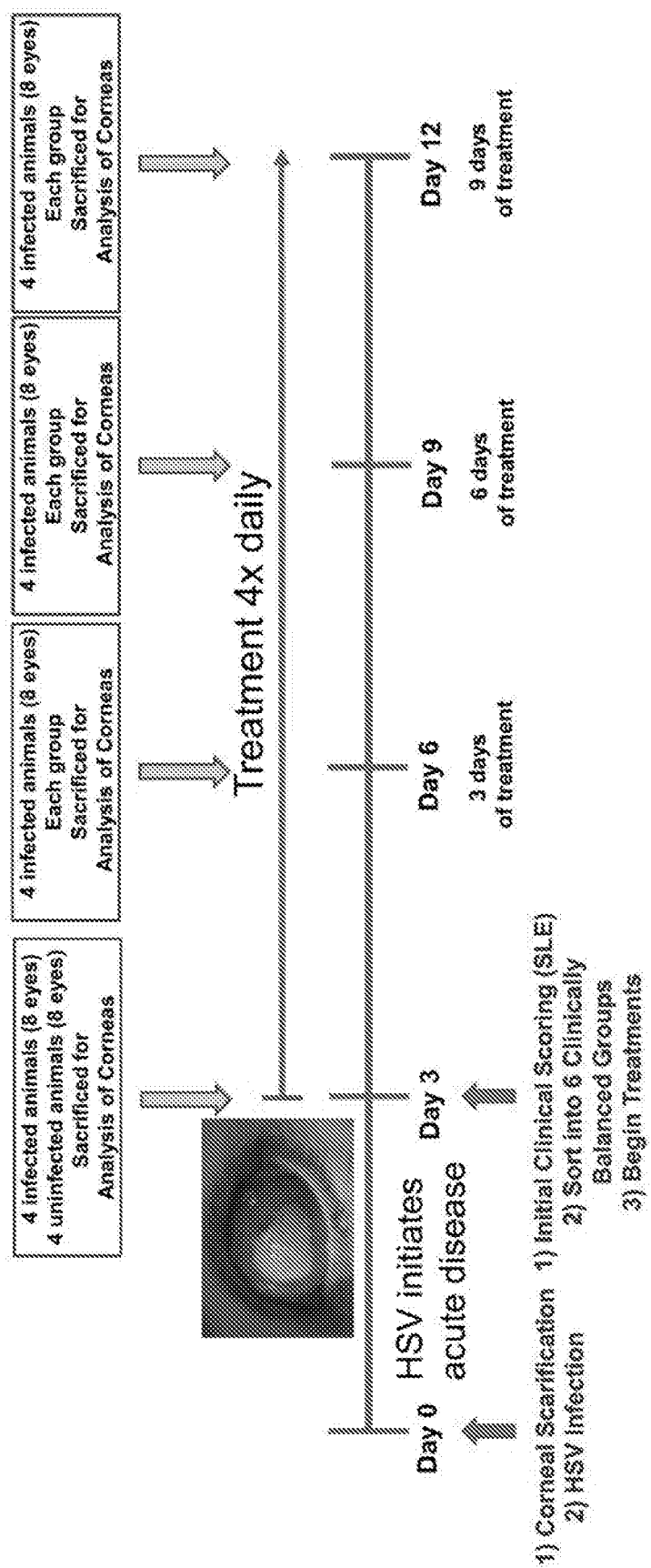
FIG. 11 shows an exemplary protocol for testing the effect of a treatment on herpes keratitis in a preclinical model. Day 0: Corneal scarification and HSV infection. Day 3: Initial clinical scoring, sorting into 6 clinically balanced groups, and treatment begins. 4 uninfected animals sacrificed and (8 eyes analyzed), and 4 infected animals sacrificed (8 eyes analyzed). Animals are treated 4 times daily and a group of 4 animals are sacrificed (8 eyes analyzed) on days 6, 9, and 12.
Figure 12:
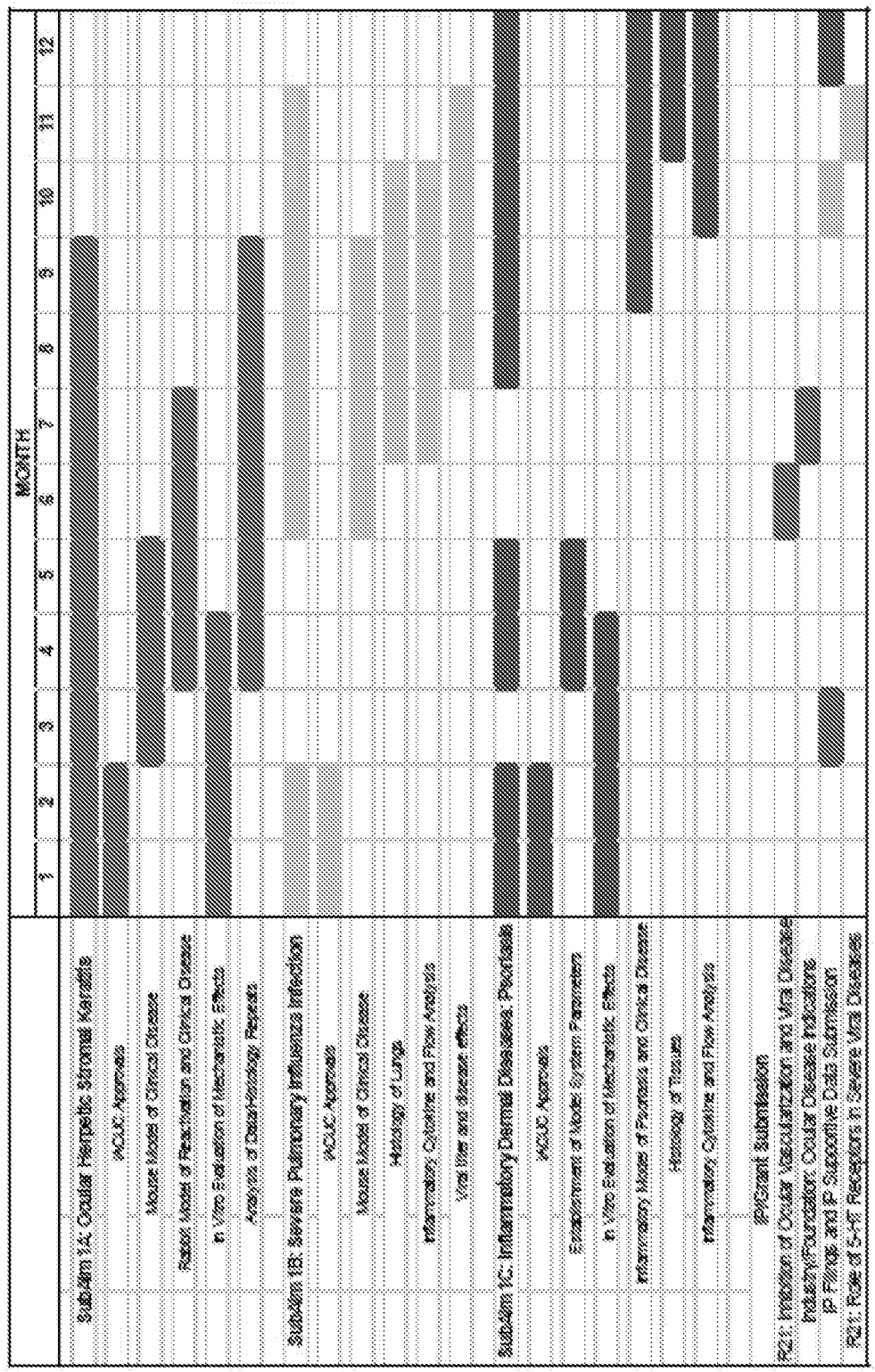
FIG. 12 is a timeline for an exemplary research plan.

The rabbit eye is an FDA accepted ocular preclinical model that accurately reflects clinical disease parameters and predicts a drug's potential for clinical resolution of human disease sequelae. In addition, the rabbit eye is the definitive clinical model for examining HSV replication and its associated disease manifestations. Drug treatment parameters can be evaluated in the rabbit herpetic eye disease model scoring clinical parameters daily as defined in FIG. 10 and the protocol depicted in FIG. 11.

Example 3: Formulation Development and Validation

Aspects of the invention are directed towards DOI, a 5-HT$_2$R agonists that can treat herpetic keratitis. In studies, (R)-DOI demonstrated anti-vascularization properties in mouse models of primary and chronic herpetic keratitis. In addition, in ex vivo neuronal models, (R)-DOI inhibited HSV-1 reactivation from latency, a main contributor to development of recurrent herpetic stromal keratitis. Without wishing to be bound by theory, experiments described herein (i) show that (R)-DOI ameliorates vascularization associated with herpetic keratitis, (ii) develop formulation and dosing parameters for effective (R)-DOI ophthalmic delivery, and (iii) establish a CNS safety profile for ophthalmic (R)-DOI.

Ophthalmic Formulation Tolerability and Pharmacokinetic Parameters of (R)-DOI

A series of experiments designed to determine dosing parameter are performed, including ocular tolerability of (R)-DOI in topical formulation, drug distribution and pharmacokinetic evaluation of (R)-DOI in the rabbit eye. This information is used to investigate therapeutic efficacy of (R)-DOI relative to the current standard of care antiviral (trifluorothymidine; TFT) and anti-inflammatory (dexamethasone) treatments.

The establishment of a drug's toxicity, safety and tolerance profiles is a prerequisite to subsequent efficacy trials. These profiles dictate a drug's practical concentrations, and properties they impart to carrier formulations that may alter tolerability (i.e., pH). In the exposed epithelium of the eye, which has regenerative and wound healing capacity that are critical for proper eye function, a drug formulation should not: 1) exhibit cellular toxicity to the corneal epithelium; 2) diminish cellular metabolic activity; 3) alter ocular physiological pH, which can burn the cornea; 4) inhibit replicative capacity of stem-like cells from the corneal limbus; or 5) impair epithelial migration/wound healing.

The rabbit remains the species of choice for the evaluation of ophthalmic compounds providing a relatively reliable model for the evaluation of ocular pharmacokinetics. Topical administration is the route of choice for the treatment of anterior segment diseases, most often with a local therapeutic effect. This route is non-invasive, painless and fast acting. In addition, the lower dosing requirements limit a drug's systemic effects. Topical bioavailability is, however, often limited due to the precorneal loss increasing drug clearance and the corneal barrier limiting the distribution of drug. The absorption, drug distribution, and localized concentrations of (R)-DOI over time in conjunctiva, aqueous humor (AH), and cornea following ocular topical delivery on the rabbit eye will guide determination of clinical doses and posology in therapeutic paradigms of keratitis and across species. The study of the ability of (R)-DOI to penetrate and distribute across the different depth of ocular matrices posterior to cornea of the eye also informs additional potential therapeutic indications, such as Uveitis. Further, describing pharmacokinetics in ocular target tissues is a challenge considering the eye's complex anatomy and its dynamic physiological protection. During drug development, animal and human pharmacokinetics can be assessed by sampling plasma at different time points. Determination of the levels of systemic exposure to (R)-DOI in the rabbit following ocular topical delivery will therefore inform future development studies where systemic exposure is of scope, and where plasma pharmacokinetics but not biopsies of the eye matrices for drug determination will be performed.

Overall Assessment Groups and Parameters

For both the pharmacokinetic study and the tolerability study, conscious Dutch-Belted rabbits (see Vertebrate Animals document) are administered test compound by topical application to the ocular surface of both eyes. 50 µL of formulated test article is administered using a calibrated pipet. The lower eyelid is pulled slightly off the ocular surface to act as a pocket and then released ~15 seconds after administration. The vehicle for formulation is 0.5% carboxymethylcellulose (CMC) in saline.

Sub-study 1: Examination of the potential ocular tolerability in male Dutch Belted rabbits following topical administration of (R)-DOI.

Experimental Approach: The ocular tolerability of 3 (R)-DOI doses (low, mid- and high (100, 300, 1000 µM)) is characterized, and vehicle alone following topical administration of the test formulation to both eyes 3 times daily (TID) for 4 days (N=2 rabbits/group, n=4 eyes/group, 50 µl per eye, for a total of 8 rabbits on study; Table 4). Draize scoring is conducted pre-dose and on days 1, 3, & 5. Full ophthalmic exams are performed pre-dose and prior to euthanasia on day 5. Eyes are enucleated and fixed for histopathology.

TABLE 4

| Test Group | Article | Route and Dose/Eye | Rabbits | Draize | Ophthalmic Exam | Terminal TimePoint |
|---|---|---|---|---|---|---|
| 1 | R-DOI | Topical, "Low" both eyes TD for 4 days | N = 2/group | Predose and Days 1, 3, & 5 | Slit lamp and indirect ophthalmoscope of the front and back of the eye by a veterinary ophthalmologist. Exams are performed predose and at Day 5 using the McDonald Shadduck Scoring System | Day 5 |
| 2 | R-DOI | Topical, "Low" both eyes TD for 4 days | | | | |
| 3 | R-DOI | Topical, "Low" both eyes TD for 4 days | | | | |
| 4 | Vehicle | Topical, "Low" both eyes TD for 4 days | | | | |

This objective establishes foundational criteria of tolerability and toxicity to the eye of a range of doses of (R)-DOI and the functional parameters that can be employed within all subsequent in vitro and in vivo studies. Success of this objective relies on the determination of the (R)-DOI concentration range in a topical ophthalmic formulation that is compatible with therapeutic effects. Future studies including experimentation with a scratch wound healing model and a radial wound-healing model will be carried to determine tolerability and acceptable use of (R)-DOI to the damaged eye.

Alternative Approaches:

A potential limitation of ophthalmic drugs is low tolerability in ocular tissues. However, effective doses of R-DOI are low (in the 100-500 µM range) and reduce the likelihood of irritability or pH-changing properties for short durations. Significantly longer chronic administration can result in tolerability issues, especially if the drug accumulates in ocular tissues upon repetitive administrations. To address this, the determination of ocular pharmacokinetics and parameters, such as area under the curve (AUC) levels and half-life, inform dosing regimen for repeated drug administration aimed at achieving near-steady-state drug levels in target ocular tissues (rate of drug elimination compensates the rate of drug administration).

Sub-Study 2: Topical Ocular Pharmacokinetic Study in Male Dutch Belted Rabbits Using (R)-DOI as a Treatment for Herpetic Keratitis.

Experimental Approach:

The ocular exposure of (R)-DOI following a single ocular topical administration of the test formulation to both eyes is characterized. Doses are administered one time to both eyes of each rabbit. Animals are euthanized immediately prior to the following time points: 0.25, 0.5, 1, 3, 6, & 24 hours post-administration. Precise dissection and processing of ocular tissues conjunctiva, iris-ciliary body, vitreous humor, retina, choroid and cornea will be performed, and aqueous humor (anterior chamber), and plasma are collected from each animal for determination of drug levels. Two animals (n=4 eyes) are used at each time point for a total of 12 rabbits. Chromatography-tandem mass spectrometry (LC-MS/MS) method development and set-up for sample analysis of plasma and ocular matrices for (R)-DOI will employ n=144 ocular samples (24 eyes×6 matrices) and n=12 plasma samples.

This study estimates first dose pharmacokinetic parameters (i.e. Tmax, Cmax, AUC0-t, AUC-∞, T1/2, CL) of ophthalmic administration of (R)-DOI in ocular conjunctiva, iris-ciliary body, vitreous humor, retina, choroid, cornea, aqueous humor, and plasma in a model closely relevant to humans.

Alternative Approaches:

The determination of drug concentrations in different matrices is subject to the sensibility, linearity, quantifying and detection limits of the analytical methods employed during the study. LC-MS/MS analytical technology of drug quantification is considered one of the most appropriate approaches for that end. It offers analytical specificity superior to that of conventional high performance/pressure liquid chromatography (HPLC) for low molecular weight analytes and has higher throughput than gas chromatography-mass spectrometry (GC-MS). The preliminary estimate limit of detection (LOD), limit of quantitation (LOQ), and upper limit of linearity (ULOL) are in the range of 5-1000 ng/ml. In this study, (R)-DOI is administered at a single dose superior to the high therapeutic dose but inferior to the maximum tolerated ocular dose for acute single administration.

Validation that (R)-DOI Controls Clinical Manifestations Associated with Both Acute and Chronic Herpetic Keratitis Using Three Complementary Animal Models Mouse model data indicates therapeutic efficacy at preventing formation of blinding herpetic stromal keratitis. Mouse studies are performed, specifically examining therapeutic efficacy in models that are directly relevant to human clinical herpes-associated chronic and recurrent disease. In addition, these studies are complemented by examining therapeutic efficacy in an acute herpetic keratitis rabbit eye model, a model that has demonstrated predictive ability in development of topical ocular therapeutics for viral- and inflammation-mediated diseases.

These studies can establish efficacy, optimal ocular delivery, and dosing parameters for a new treatment approach to herpetic keratitis. These studies validate the use of embodiments of the invention for other inflammation-associated ocular diseases.

Development of herpetic keratitis is due both to viral and host-mediated processes, which result in chronic and recurrent disease manifestations that are not effectively controlled by current antiviral therapeutics. This strategy validates (R)-DOI's ability to control disease manifestations associated with acute, chronic, and recurrent herpetic keratitis without the deleterious consequences associated with anti-inflammatories, such as uncontrolled viral replication and increased intraocular pressure in three sub-studies.

Overall Assessment Groups and Parameters:

Each of the sub-studies follows a similar experimental design outline with five arms (summarized in Table 5) that will assess the effect of two doses of (R)-DOI relative to: 1) control BSS treatments; 2) an antiviral drug (TFT); or 3) anti-inflammatory dexamethasone. All treatment groups are masked by color coding. For each sub-study, separate clinical, behavioral, and virological assessments are scored daily by independent investigators masked to treatment. At the end of each sub-study protocol, eyes are enucleated, and histopathology is performed.

TABLE 5

| Assessment Arm | Drug Treatment Group | Dose; Administration |
| --- | --- | --- |
| Treatment Control | Ophthalmic BSS | BSS; Topical |
| Antiviral | Trifluorothymidine (TFT) | 1%; Topical |
| Anti-Inflammatory | Dexamethasone | 0.1%; Topical |
| Test High R-DOI | R-DOI in BSS | 500 µM; Topical |
| Test Low R-DOI | R-DOI in BSS | 5 µM; Topical |

Sub-study 1: Determining the Therapeutic Efficacy of (R)-DOI for Resolution of Acute HSV Keratitis in a Rabbit Eye Model.

The rabbit eye model of HSV-1 infection has been established as a gold-standard small-animal model assessment of a drug's ability to affect HSV-mediated acute ocular disease. The rabbit eye model of acute HSV-1 infection closely mimics the virological, as well as neovascularization-associated clinical parameters of a human infection. Unlike other studies in the mouse eye, the rabbit eye is in many respects more morphologically similar to the human eye and viral replication and the acute herpetic keratitis disease course ensues like human disease. As such, it has been shown to robustly predict pharmaceutical efficacy of topical therapeutics. Ocular pharmacological parameters established above can be correlated with disease outcomes and utilized to optimize future dosing and treatment regimens.

Experimental Approach:

New Zealand White rabbits (7 per treatment group; n=14 eyes) have the corneas of both eyes scarified in a 4×4 cross-hatched pattern and immediately inoculated with $3 \times 10^5$ PFU of HSV-1 suspended in 50 µl of ophthalmic BSS. To assess treatment effects on infection resolution and clinical disease, infection proceeds unabated for three days, at which time animals will be clinically scored and accordingly sorted into clinically balanced groups prior to beginning treatment. This process normalizes inherent differences between animals and recapitulates the clinical scenario of a person reporting to the clinic with the onset of herpetic lesions. Topical drugs are administered four times daily. As depicted in Table 3, each morning scores for each clinical disease parameters are assessed by slit lamp biomicroscopy. In addition, intraocular pressure is determined each morning and just prior to last treatment using a Tonovet rebound tonometer. Infectious virus is collected from the tears daily in order to assess drug effects on viral replication. To determine if drug treatments have any deleterious effects on behavior, the behavior is monitored according to the parameters defined herein, briefly prior to each treatment and for a continuous 15 minutes following last daily treatment. At the end of the acute disease study, histological assessment of the eye will be performed to visualize what has been scored clinically and virologically.

Sub-study 2: Determining the Therapeutic Efficacy of (R)-DOI for Prevention of Acute and Chronic HSV Keratitis in a Mouse Eye Model.

Although the acute rabbit eye model effectively assesses virological, clinical and pharmacological parameters of drug studies, the acute model does not efficiently permit assessment of chronic host-mediated factors that contribute to herpetic stromal keratitis. Infection of BalbC mice with HSV-1 (RE) strain results in nearly 100% of animals developing blinding herpetic stromal keratitis, with a large percentage developing disease despite effective suppression of viral replication by antivirals. Therefore, this model is used to assess the effects of (R)-DOI on host-mediated chronic HSV-associated ocular disease development.

Experimental Approach:

9-week-old Balb/C mice (10 mice per group; n=20 eyes) have the corneas of both eyes scarified in a 4×4 cross-hatched pattern and immediately inoculated with $5×10^3$ PFU of HSV-1 (RE) strain suspended in 5 µl of ophthalmic BSS. Animals are randomly assigned to treatment groups as in Table 3 and drugs or specific controls will be administered four times daily beginning at three hours post-infection. Daily clinical, behavioral and virological assessments beginning at 24 hours post-infection until day 10 will be performed. At approximately 8-9 days post-infection, viral titers are nearly undetectable in surviving animals and the host-mediated disease processes start. After the initial 10 days, clinical and virological assessments continues every other morning until 20 days post infection upon which scoring the clinical disease parameters described herein by slit lamp biomicroscopy is performed. Twenty days post-infection represents the time of peak chronic disease, thus animals are sacrificed and eyes removed for histological examination. Infiltration of specific immune cells, vascularization, thickening of stroma and epithelium, and fibrotic scarring will be examined.

Sub-study 3: Determining the Therapeutic Efficacy of (R)-DOI for Prevention of Recurrent Herpetic Keratitis in a HSV-Latency Reactivation Mouse Model.

Blinding herpetic stromal keratitis in humans occurs following years of HSV reactivation and recrudescent ocular disease. Although they have their usefulness in determining drug efficacy, the primary HSK models described herein do not recapitulate some aspects of HSK, which occur as a result of reactivating in the context of an immune host that developed an adaptive immune response against HSV. Therefore, this model assesses the effects of (R)-DOI following HSV reactivation and development of recurrent immune-mediated disease.

Experimental Approach:

To reduce mortality and prevent acute HSK during the primary infection, $C_{57}BL/6$ mice (15 mice per group; n=30 eyes) are IP administered normal human immunoglobulin prior to infection. The corneas of both eyes are scarified in a 4×4 cross-hatched pattern and immediately inoculated with $1×10^6$ PFU of HSV-1 McKrae strain suspended in 5 µl of ophthalmic BSS. Six weeks following primary infection, eyes are scored and animals with eyes that do not exhibit signs of ocular disease will be randomly sorted into assessment groups as described herein. HSV is reactivated by exposure to UV-B light with a transilluminator, tear film collected for the presence of virus, and treatments begins. Mice are evaluated by a masked observer every 5 days for 25 days, at which time animals are sacrificed and the eyes are removed for histological examination.

Metrics of Success and Alternative Approaches:

(R)-DOI suppresses deleterious HSV-induced disease in these models of herpetic keratitis. (R)-DOI can be effective at suppressing disease sequelae associated with acute, chronic and recurrent HSK without increasing HSV replication or intraocular pressure.

Example 4. Development

Pathological vascularization and dysregulation of vascular function are critical determinates in the outcomes of many diseases, such as viral-mediated pathologies, cancer, rheumatoid arthritis, psoriasis, and severe pulmonary infections. In addition, pathological vascularization within the eye, and especially within the normally avascular cornea, is the main contributor to many ocular diseases, including blinding stromal keratitis, proliferative retinopathies, and macular degeneration. Studies described herein determine the therapeutic viability and effectiveness of $5-HT_{2A}$ agonists in resolving vascularization-associated disease processes of the eye.

I. Determining the ocular toxicity, safety, and tolerance of $5-HT_{2A}$ agonist therapeutic formulations.

Toxicity, safety, and tolerance profiles inform a drug's practical concentrations, therapeutic indexes, and properties they impart to carrier formulations that may alter tolerability. In the exposed epithelium of the eye, which has regenerative and wound healing capacity that is critical for proper eye function, additional criteria must be met. A drug formulation should not: 1) exhibit cellular toxicity to the corneal epithelium; 2) diminish cellular metabolic activity; 3) alter ocular physiological pH, which can burn the cornea; 4) inhibit replicative capacity of stem-like cells from the corneal limbus; 5) impair epithelial migration/wound healing. This study establishes these foundational criteria and the functional parameters that can be employed within all subsequent in vitro and in vivo studies. It also serves as the evaluation criteria for the institutional animal use panels.

Sub-study 1A: Establishing prerequisite ocular cytotoxicity and effects on ability to repair wounds for $5-HT_{2A}$ agonist formulations.

In vitro evaluation of toxicity is demonstrated by evaluating cytotoxicity to corneal epithelium, scratch wound repair of corneal epithelium, and radial wound repair of corneal epithelium. Given the nature of the eye, for topical ocular drops, measuring cytotoxicity to corneal epithelium involves a multi-parameter assessment including, direct cellular toxicity, effects on wound healing and repair, and changes to cellular proliferation and metabolic energy production.

Pharmacological Cytotoxicity Assessments to Primary Human Corneal Epithelium:
1) Dose Dependent Cellular Cytotoxicity
2) Time-Dependent Cellular Cytotoxicity (daily and long-term assessments)
3) Determination of 50% Cellular Cytotoxicity ($CC_{50}$)

Cytotoxicity Assessments and Cell Viability are Evaluated by:
1) Membrane Integrity Assays
2) Metabolic Activity Assays
3) Energy Production Assays
4) Cellular Proliferation Assays The cornea necessarily has regenerative capacity that ensures maintenance of visual acuity. Damage to the corneal epithelium is repaired through a process of cellular replication and migration from the corneal limbus "fill in" sites of damage. Drugs that inhibit these processes are inherently toxic within the eye following short-term or long-term use. Therefore, assessment of the effects of 5-$HT_{2A}$ agonists in scratch (two-dimensional migration) and radial (proliferation and multidimensional migration) wound repair models at non-cytotoxic doses is a useful safety analysis to inform subsequent in vivo testing of the same parameters.

Wound Healing Assessments:
1) Concentration-Dependent Percent Healing in 24 hours
2) Kinetics of Wound Healing
3) Ocular Drug Carrier Effects on Wound Healing Sub-study 1B: Evaluating in a rabbit eye model the in vivo toxicity and effects on wound repair for 5-$HT_{2A}$ agonist topical therapeutic formulations.

In vivo evaluation of ocular toxicity comprises irritation/draize, scratch wound repair of corneal epithelium, and radial wound repair of corneal epithelium. Daily clinical assessments include intraocular pressure, wound size, rate of closure, slit-lamp biomicroscopy, corneal neovascularization, corneal epithelium, corneal inflammation, epiphora, stromal inflammation, scleral inflammation, conjunctival inflammation, blepharitis, inflammatory discharge, behavioral toxicity.

Formulations are assessed in an escalating series of in vivo ocular toxicity models: 1) an ocular irritation model following repeated dosing; 2) a scratch wound healing model; 3) a radial wound healing model where >90% of the corneal epithelium will be removed and allowed to regenerate during repeated dosing. Ocular tissues and blood samples are collected for determination of drug distribution.

5HT2a Receptor Agonist Topical Ophthalmic Formulations:
1. Selection of topical ophthalmic carriers and non-toxic drug concentrations.
2. Determination of solubility, pH, etc. Optimization of pH.
3. Assessment of short-term maintenance of formula properties: 8 days
4. Assessment of longer-term maintenance of formula properties: 30 days Ocular Irritation Assessments Repeated Dosing (Rabbit Eye Model):
1. Short-term Acute Toxicity: 1 dose; 24 hour assessment of herein defined clinical parameters.
2. Repeated Dosing Toxicity: dosing 4-8× per day; Clinical Assessments two times per day (morning/evening) as per herein defined clinical parameters: 7 days Drug Effects on Ocular Wound Healing (Rabbit Eye Model):
1. Determination of Effects of Drug on Healing of Corneal Crosshatched Scratches
2. Determination of Effects of Drug on Healing of 10 mm Radial Corneal De-Epithelialization
3. Assessment of all clinical parameters defined herein daily Although these studies are designed to assess ocular toxicity effects of 5$HT_{2A}$ receptor agonist ophthalmic formulations, they also provide clinical information on reduction of surgical- or trauma-induced ocular neovascularization, which worsens prognosis. Furthermore, effects of these drugs on intraocular pressure may give indications for use in diseases, such as glaucoma, or as an alternative for steroidal anti-inflammatories that increase IOP.

II. Evaluating delivery, dosing, and distribution of therapeutic formulations of 5-$HT_{2A}$ agonists.

Tissue distribution and localized concentrations of 5-$HT_{2A}$ agonists following ocular topical or systemic delivery can inform additional potential therapeutic indications. This study is coordinated with the in vivo ocular safety and toxicity studies described in sub-study 1B. Following completion of all studies, eyes treated with drug concentrations that did not exhibit any ocular toxicity are harvested and the following tissues collected: 1) Cornea; 2) Conjunctiva; 3) Sclera; 4) Aqueous Humor; 5) Vitreous Humor; 6) Retina; 7) Blood/Sera. Samples are catalogued, flash frozen, and stored at −80° C. for future analysis.

A second evaluation of distribution following systemic delivery (intravenously administered through rabbit ear) is also performed at 24 and 48 hours to assess ocular distribution and concentrations following systemic administration.

III. Evaluating the therapeutic efficacy of 5-HT2a agonists for amelioration of diseases.

Infection-associated eye diseases are the leading causes of corneal blindness and visual morbidity, with over 500 million individuals affected. Pathogen-associated ocular diseases are a complex combination of pathogen-mediated trauma and host-mediated pathologies. When available for ophthalmic use, anti-pathogen drugs can inhibit a pathogen's replication and often lessen the severity of pathogen-associated disease. However, they can be specific to a given pathogen, elicit drug induced toxicity of the corneal epithelium, and target only a single aspect of a pathogen's replication machinery. For persistent or recurrent ocular infections, such as HSV-1, long term use of these drugs can result in development of drug resistant variants. More importantly, current anti-pathogen drugs fail to inhibit host-mediated neovascularization responses and therefore, ocular disease can progress despite a drug's ability to control infection. This study involves four sub-studies (3A-3D) that directly assess ocular and pulmonary indications for 5-$HT_{2A}$ agonists.

Sub-study 3A: Evaluating the therapeutic efficacy of 5-HT2a agonists in resolution of acute and chronic Herpetic Keratitis.

Analysis of viral replication: Corneas of both eyes of New Zealand White rabbits (1.5-2 kgs) are scarified in a 4×4 cross hatched pattern and immediately inoculated with 3×10$^5$ PFU of HSV-1 suspended in 50 μl of ophthalmic BSS. For prevention studies, animals are randomly assigned into treatment groups and drugs or specific controls will be administered beginning at three hours post-infection and clinical and virological assessments commence beginning at 24 hours post-infection. For resolution of infection and clinical disease, infection proceeds unabated for three days, at which time animals are clinically scored and sorted into clinically balanced groups prior to beginning treatment. This process normalizes inherent differences between animals and recapitulates the clinical scenario of a person reporting to the clinical with the onset of herpetic lesions. Topical drugs will be administered daily, such as 4-6 times daily. As depicted herein, each morning until day 9 post-infection, scores for clinical disease parameters are assessed by slit lamp biomicroscopy. In addition, intraocular pressure is assessed. Following scoring, infectious virus are collected on ocular swabs from the tears in order to assess effects on viral replication without effecting clinical outcomes. Effects on viral replication are determined by number of eyes positive for infectious virus, as well as the relative titer of virus per ocular swab for each day assessed.

Analysis of latent HSV-1: Nine-week old mice (approximately 18 g) have the corneas of both eyes scarified in a 4×4 cross-hatched pattern and are immediately inoculated with $1\times10^5$ PFU of HSV-1 suspended in 5 µl of ophthalmic BSS. Animals are randomly assigned into treatment groups and drugs or specific controls are administered beginning at three hours post-infection and clinical and virological assessments commence beginning at 24 hours post-infection. Topical drugs are administered daily, such as 4-6 times daily. Each morning until day 9 post-infection, scores for nine clinical disease parameters are assessed by slit lamp biomicroscopy and the weight of each animal is determined. Following scoring, infectious virus are collected daily on ocular swabs from the tears in order to assess effects on viral replication without effecting clinical outcomes.

For analysis of reduction of latent HSV-1 within neurons, the number of neurons and the levels of viral genomes latent within neurons can indicate the likelihood for increased episodes of reactivation and/or viral shedding. To determine the effects of treatment on the levels of HSV-1 viral genomes present within neurons following acute infection, virus will be allowed to establish latency for at least 30 days prior to any assessments and latency will be defined by two consecutive negative ocular swabs 30 days post infection. Trigeminal ganglia (TG) are removed and the levels of viral genomes per TG are determined by quantitative RT PCR relative to a standard curve. In addition, the ability of $5\text{-HT}_{2A}$ agonists to inhibit ex vivo reactivation of HSV from latent neurons is assessed.

Chronic HSV stromal keratitis: HSV-1 infections of the eye are the leading cause of infectious corneal blindness in the developed world. The disease course is due to both viral and host-mediated processes that are not always effectively controlled by ophthalmic antivirals. Although the acute rabbit eye model effectively assesses virological, clinical and pharmacological parameters of drug studies, the model does not efficiently permit assessment of contributing host-mediated disease factors that contribute to reproducible herpetic stromal keratitis. Infection of BalbC mice with HSV-1 RE results in nearly 100% of animals developing blinding stromal keratitis, with a large percentage still developing disease despite effective suppression of viral replication by the antiviral 1% TFT. A mouse model of HSV RE strain-induced stromal keratitis that has characteristics of chronic herpetic eye disease is used.

Sub-objective 3B. Evaluating the therapeutic efficacy of $5\text{-HT}_{2A}$ agonists in resolution of acute adenoviral conjunctivitis (pink-eye).

The rabbit eye model of adenoviral replication and induction of associated disease is used as the rabbit eye is a good predictor of ophthalmic drug efficacy and the associated disease outcomes mimic that observed in a human infection.

New Zealand White rabbits (1.5-2 kgs) have the corneas of both eyes scarified in a 4×4 cross hatched pattern and immediately inoculated with $2\times10^6$ PFU of adenovirus suspended in a 50 µl drop of ophthalmic BSS. Animals are randomly assigned into treatment groups and drugs or specific controls are administered beginning at three hours post-infection. Topical drugs are administered daily, such as 4-6 times daily, except that the reference control, cidofovir, is administered twice daily due to toxicity. Each morning, scores for clinical disease parameters described herein are assessed by slit lamp biomicroscopy. In addition, intraocular pressure is assessed. Following scoring, infectious virus are collected on ocular swabs and titered on A549 cells to assess effects on viral replication.

Given the viral- and host-mediated complexities of adenovirus-induced eye disease the endpoints of this model include daily assessments of drug effects on both viral replication and neovascularization-associated clinical disease. Effects on viral replication will be determined both by number of eyes positive for infectious virus, as well as the relative titer of virus per ocular swab. Histological assessment of the eye at day 8 are performed to visualize what is scored clinically and virologically.

IV. Validation of anti-neovascularization activities of $5\text{-HT}_{2A}$ receptor agonists.

This study confirms that $5\text{-HT}_{2A}$ receptor agonists directly affect neovascular/angiogenic processes. This objective is accomplished through three complementary sub-studies:

Sub-study 4A: Assessing the effects of $5\text{-HT}_{2A}$ agonist formulations on expression of mediators of neovascularization (e.g., VEGF, nitric oxide, cytokine, and chemokine arrays).

Treatment with $5\text{-HT}_{2A}$ receptor agonists can suppress expression of specific mediators of neovascularization. Effects of $5\text{-HT}_{2A}$ receptor agonists on production of mediators of vascularization is assessed. Specifically, (1) vascularization-associated PCR arrays are utilized to assess the relative transcriptional profiles of genes associated with these disease promoting pathological processes following treatment and stimulation with various inducers. These arrays include analysis of growth factors and their receptors, signaling pathways, cell cycle regulatory pathways, cytokines and chemokines, adhesion molecules, proteases, and matrix proteins. These arrays also provide statistical analysis of how $5\text{-HT}_{2A}$ receptor agonists affect transcriptional expression of genes in these pathways; (2) multiplexed quantitative protein analysis of secreted proteins is performed via Bioplex following treatment and stimulation by various inducers that are associated with disease progression or poor prognosis. This work may be coupled with in vivo studies to yield additional mechanistic information on the anti-neovascularization activity; and (3) nitric oxide and/or other reactive oxygen species involved in dysregulated vascular processes is assessed from treated and stimulated macrophage and/or dendritic cell lineages.

Sub-objective 4B: Identifying $5\text{-HT}_{2A}$ agonists as direct suppressors of neovascularization/angiogenesis within in vitro and ex vivo models of vaculogenesis.

For example, $5\text{-HT}_{2A}$ receptor agonists can abrogate endothelial cell migration, vessel sprouting, tube formation, and stabilization. Effects on endothelial cell migration are assessed. Migration of vascular endothelium is essential for formation of new vasculature. The ability $5\text{-HT}_{2A}$ receptor agonists to inhibit primary HUVEC & HMVEC migration is assessed via scratch wound healing assays and transwell migration assays.

Wound healing migration assay: Confluent monolayers of HUVEC or HMVEC cells are treated with $5\text{-HT}_{2A}$ receptor agonists and a scratch wound is induced in a cross pattern using a pipette tip. Cells are microscopically imaged in real time every 30 minutes for 24 hours on a live cell imager. The percent closure and kinetics of closure are determined and the ability of cells to migrate and to form podia and cell extensions are assessed from videos.

Transwell migration assay: Cells are seeded into the upper chamber of a transwell with VEGF maintained in the lower chamber to facilitate a chemotactic gradient. Wells are either be treated with 5-$HT_{2A}$ receptor agonists or controls and 24 hours later, cells that have migrated through the transwell are imaged and quantified.

Effects on vessel sprouting and tube formation are assessed. The ability of DOI to directly affect vessel sprouting and tube formation is assessed in a matrigel tube formation assay and an aortic ring sprout and vascularization assay. Matrigel containing 5-$HT_{2A}$ receptor agonists or controls are solidified onto 48 well plates. Vascular endothelial cells form 3D vascular tubes when plated onto matrigel. After 12 and 24 hours, cells are imaged and the extent of vascular tube formation, tube thickness, and branch points are quantified using WimTube/Wimasis image analysis package. For the aortic sprouting assay, a mouse aorta is removed and cut into 1 mm sections. The aorta is placed upon the initial matrigel layer and overlayed with additional matrigel containing 5-$HT_{2A}$ receptor agonists or controls. Aortas are imaged daily using a stereomicroscope and quantified for: 1) initiation of vessel sprouting; 2) length of sprouts; 3) number of sprouts; 4) number of branch points.

In vivo studies demonstrate that vascularization of the sclera and cornea had already occurred prior to beginning treatment. Therefore, 5-$HT_{2A}$ receptor agonists may not only inhibit progression of vascularization, but may resolve regions of neovascularization as indicated by a marked lessening of branch structures and a thinning of size and density of vessels. This may be due to the ability of 5-$HT_{2A}$ receptor agonists to destabilize endothelial cell attachments, branch structures and vascular smooth muscle cell stabilization of vessels. To assess the destabilization activity of 5-$HT_{2A}$ receptor agonists, aortic rings are allowed to grow tube structures with multiple branch points (these rings can be derived from control rings herein). Rings and tube structures are imaged and treated in growth factor media containing 5-$HT_{2A}$ receptor agonists or controls. The effects of 5-$HT_{2A}$ receptor agonists on maintenance of the branch points and tube structures are imaged daily over seven days and changes in tube structures, tube length, and branch points will be determined quantitatively. After seven days, rings and their attached structures are fixed and a final assessment of structural integrity/stability is determined by staining with smooth muscle actin, DAPI, and extracellular markers. Tubes are imaged by deconvolution fluorescent microscopy and analyzed for overall differences in integrity, branch point stabilization, length of vessels, and presence of SMA markers surrounding formed tubes.

Sub-objective 4C: Validating the direct therapeutic potential of 5-$HT_{2A}$ agonist formulations in suppressing neovascularization/angiogenesis in non-inflammatory VEGF-corneal implant and matrigel plug implant in vivo models.

Infectious and biochemical models described herein are utilized to determine if 5-$HT_{2A}$ receptor agonists can prevent and resolve pathological vascularization. However, the nature of these studies precludes assignment of direct anti-vascularization activity as they are complicated by the ability of 5-$HT_{2A}$ receptor agonists to inhibit viral replication. VEGF is involved in inducing pathologic angiogenesis and increased vascular permeability in several serious eye diseases and in cancer. It is therefore assessed whether DOI can directly block VEGF-mediated neovascularization in two complementary and directly translatable model systems: 1) in a VEGF-mediated ocular vascularization model that has become a standard for evaluating a drug's anti-vascularization activity; 2) in a matrigel implant tumor vascularization model that will assess the ability of locally and systemically administered DOI delivery to block vascularization of a disease tissue.

(i) Validation of DOI as a suppressor of VEGF-mediated ocular neovascularization and its associated pathology following implant of a slow-release VEGF pellet within a rabbit corneal micropocket.

A rabbit corneal micropocket assay is used to assess the ability of topically administered DOI to prevent VEGF-mediated corneal vascularization. VEGF or saline control slow release micropellets are generated as described previously. A corneal micropocket is created in each rabbit eye 3.0 mm from the corneal limbus, and micropellets are implanted. Starting the day after implant, paired OD and OS eyes are treated four times daily with either control (OD eyes) or DOI (OS eyes) drops, respectively. The utilization of sister eyes for topical drug evaluation controls for animal-to-animal variability. Eyes are clinically assessed daily and imaged by slit lamp biomicroscopy as described in all other ocular studies herein.

The daily area of corneal neovascularization is determined by measuring the vessel length (L) from the limbus; the number of clock hours (C) of limbus involved; and the radius of the cornea (r). The amount of vascularization present in each eye on each day is calculated by the formula: $A=C/12 \times 3.1416 \ (r^2-(r-L)^2)$.

VEGF-induced vascularization and vessel permeability can lead to corneal edema, inflammation, and ocular clouding. Therefore, a panel of clinical parameters (described herein) is assessed daily by fluorescent slit-lamp biomicroscopy to ascertain the therapeutic effects of topical DOI treatment on vascularization-mediated eye disease.

Eyes treated with DOI not only showed a resolution of vascularization, but clinical presentation of edema and chemosis were greatly reduced. VEGF is a known mediator of vascular permeability and we have observed in this model system that edema and chemosis is common, irrespective of the extent of vascularization induced. To ascertain the effects of DOI on VEGF-mediated vascular leakage, FITC dextran is systemically delivered via the ear vein and its presence is assessed in the cornea, conjunctiva and sclera by fluorescent biomicroscopy. If visual examination shows clear indication that DOI suppresses vascular leakage by the relative absence of FITC within ocular tissues, animals are sacrificed, corneas are removed, and the relative levels of FITC are determined spectrophotometrically following tissue homogenization and digestion. Representative eyes are processed for histology for direct visualization of extent of ocular vascularization and presence of edema.

(ii) Validating DOI as a suppressor of angiogenesis and vascularization of a matrigel plug implant in a tumor vascularization model.

Most anti-vascularization therapies are being developed to inhibit vascularization of solid tumors. This study expands the evaluation of the ability of 5-$HT_{2A}$ receptor agonists to suppress angiogenesis and pathological vascularization, while simultaneously evaluating its effectiveness at suppressing vascularization following local or systemic delivery. Matrigel is infused with VEGF (and/or PDGF) and either combined with 5-$HT_{2A}$ receptor agonists or a control treatment. The resulting paired suspensions are injected subcutaneously into each mouse flank and allowed to polymerize. Seven-to-ten days post-implant, mice are sacrificed and the extent of vascularization into the matrigel is assessed. In a parallel experiment, untreated growth factor-infused matrigel is implanted and either 5-$HT_{2A}$ receptor agonists or controls are delivered systemically by subcutaneous injection each day to evaluate whether systemic delivery can suppress vascularization of the matrigel implant.

The ability of localized and systemic delivery of 5-HT$_{2A}$ receptor agonists to thwart growth factor-induced vascularization of the matrigel implant is assessed by: 1) direct visualization and imaging of the blood content present between the two treatments (matrigel is clear if no vascularization); 2) quantifying the amount of hemoglobin present within the excised implants using Drabkins reagent; 3) immuno-histopathological examination of sections of the plug with CD34 staining of the vascular endothelium; 4) FITC-dextran injection into the tail vein followed by excision of the explant and confocal 3D imaging of vascularization and extent of branching.

Example 5: Aortic Ring Assay

Figure 13:
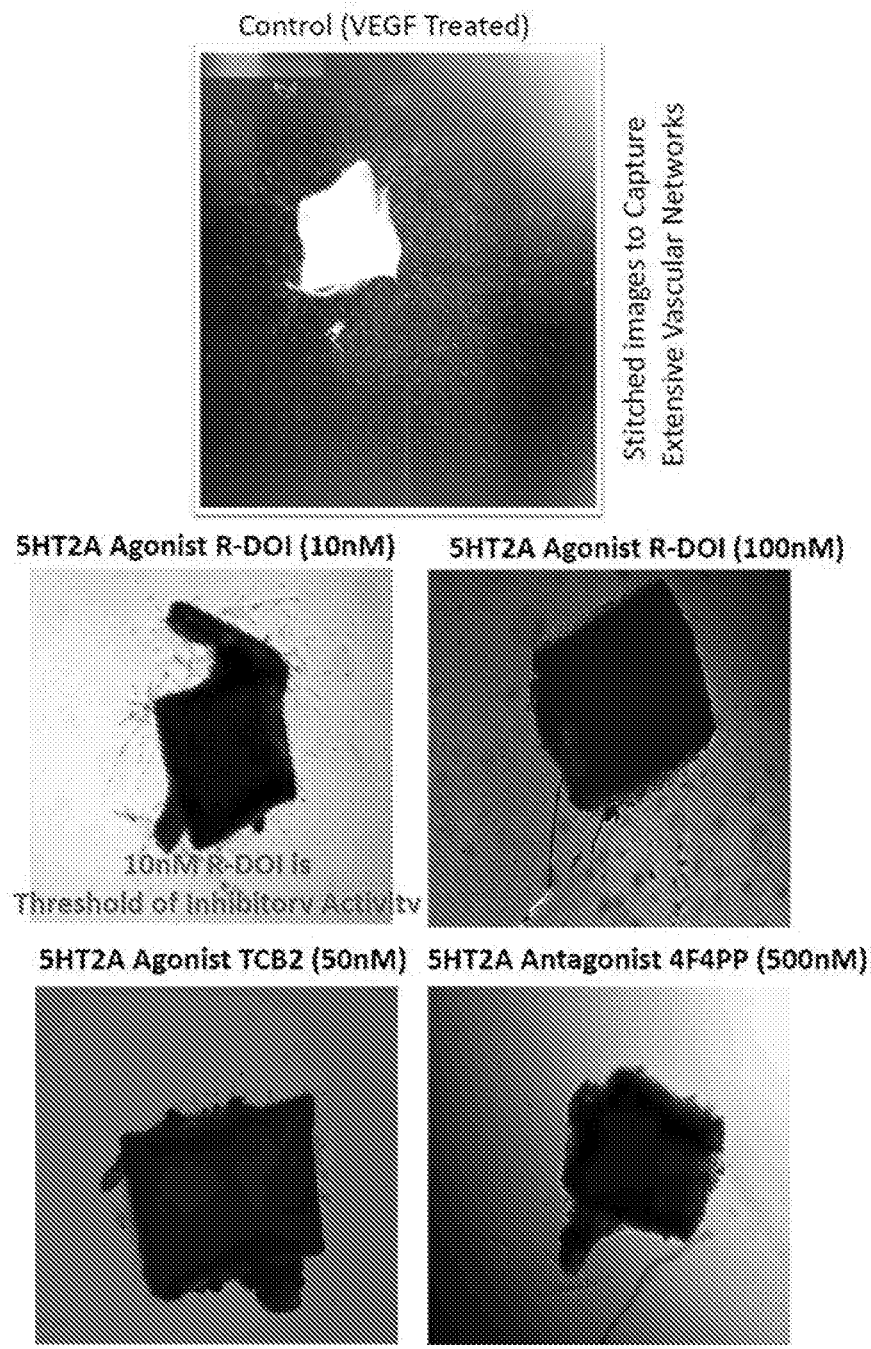
FIG. 13 is a series of photographs showing VEGF-mediated neovascularization from aortic rings in the presence of R-DOI, TCB2, and 4F4PP.

Aortas from sacrificed mice are removed, cleaned, and dissected into 1 mm tubule sections, as shown in FIG. 13. These aortic rings are implanted into matrigel basement membrane and incubated in endothelial cell growth medium containing vascular endothelial growth factor. Aortic rings are continuously incubated in the presence of 5-HT$_{2A}$ receptor agonists and antagonists at the indicated concentrations and examined by microscopy daily. Extensive sprouting, branching and networking of new blood vessels can be observed in control aortic rings, where multiple images needed to be stitched together in order to capture the extensive blood vessel network formed.

By contrast, 5-HT$_{2A}$ agonists (R-DOI and TCB2), inhibited blood vessel sprouting, branching and formation. It was also determined that ata 10 nM concentration of R-DOI, the inhibitory effects for neovascularization, sprouting, branching, and networking began to no longer be as effective.

Example 6: Endothelial Tubule Formation Assay

Figure 14:
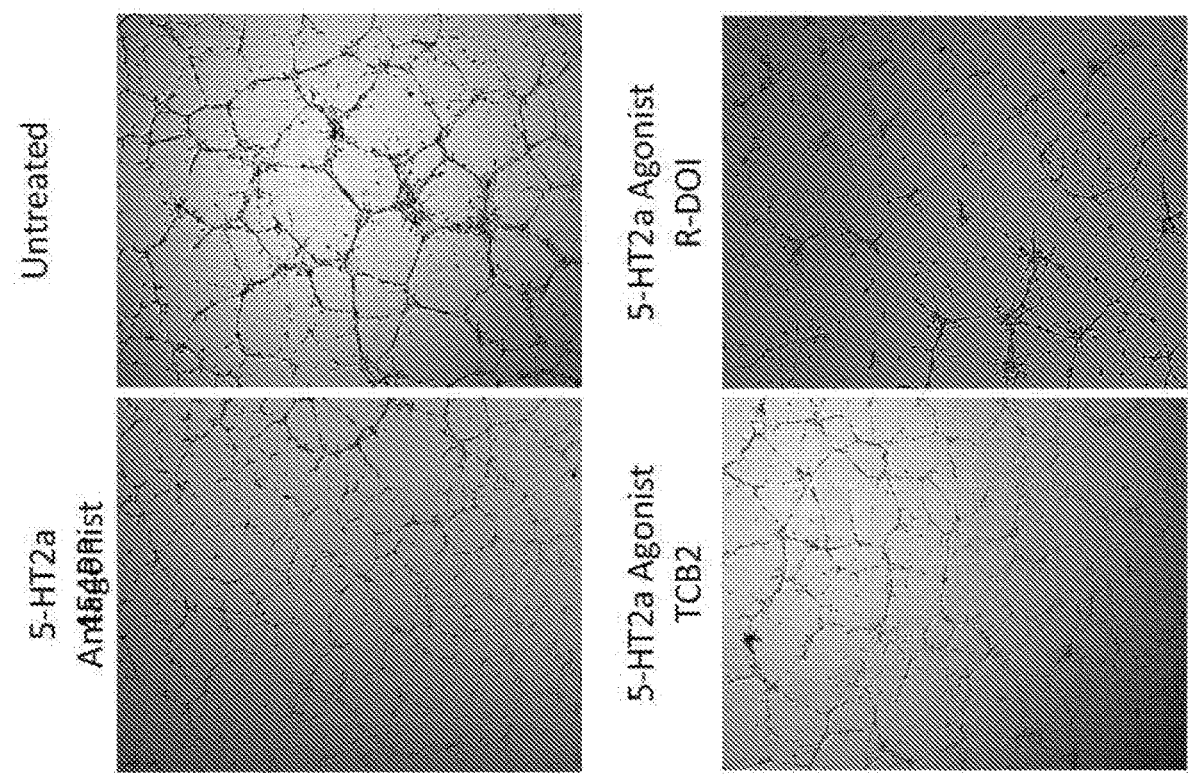
FIG. 14 is a series of photographs showing VEGF-mediated human vascular endothelium tubule formation in the presence of R-DOI, TCB2, and 4F4PP.

To assess the ability of 5-HT$_{2A}$ agonists and antagonists to inhibit capillary-like endothelial tube formation, human microvascular endothelial cells were seeded into geltrex basement membrane and overlaid with endothelial growth medium containing vascular endothelial growth factor (VEGF) and the indicated drugs. As shown in FIG. 14, 5-HT$_{2A}$ agonists and antagonists disrupted formation of endothelial tube networks, the formation of branching, complex capillary structures, and interconnectivity of capillary tubes.

Example 7: Inhibition of HSV-1 Neuronal Reactivation from Latency within Trigeminal 14 trigeminal ganglia from 7 ocularly infected mice that contained latent HSV-1 genomes within its neurons for greater than 60 days were removed, randomly divided into 2 groups of 7 ganglia, and were subsequently explanted and eviscerated in media that contained either 500 nM of DOI or an equivalent buffer control without drug. HSV-1 reactivation from latent neurons was induced using hyperthermic shock (42C) for 1 hour. Each day for 10 days post explant and induction of reactivation, ⅕ volume of media volume was removed and assessed for the presence of infectious HSV-1, indicating reactivation of virus from latency. This volume was replaced with media that contained either 500 nM of DOI drug or an equivalent of mock carrier buffer.

As shown in Table 6, the 5HT agonist, DOI, maintains latency of HSV-1 within reactivation induced neurons as observed by the number and percentage of neurons positive for the presence of any infectious HSV-1. In addition, there was a significant delay in reactivation (2 fold greater) of HSV-1 from TGs that showed slight positivity for eventual presence of infectious virus.

Figure 15A:
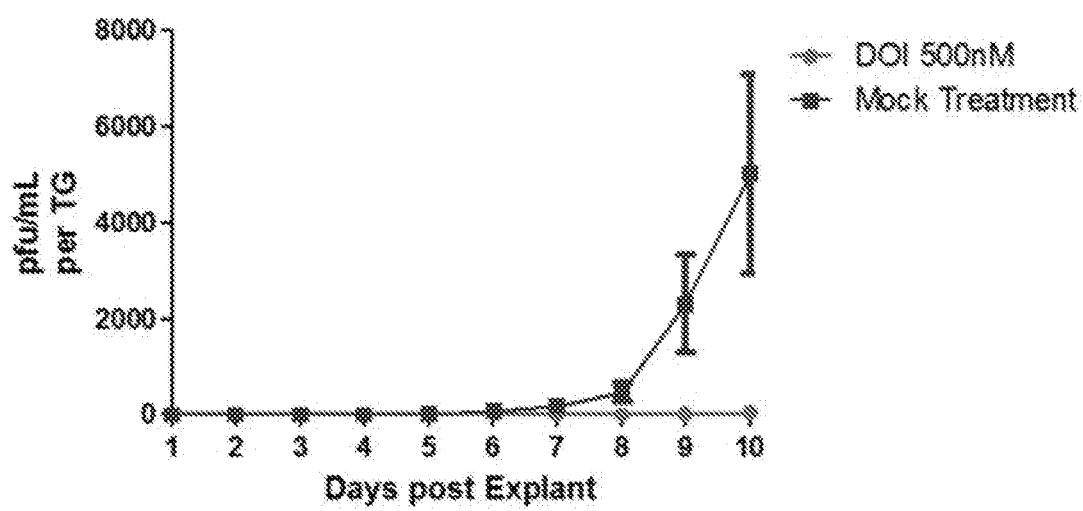
FIGS. 15A and 15B are graphs showing that R-DOI inhibits HSV-1 reactivation from latent neurons within the trigeminal ganglia (TG). Reactivation of latent HSV-1 was induced from TG explants from mice previously ocularly infected with HSV-1. Ganglia were either treated with control (Mock treatment; blue) or media that contained 500 nM (R)-DOI (DOI 500 nM; red). The presence of infectious HSV-1 was assessed for 10 consecutive days.
Figure 15B:
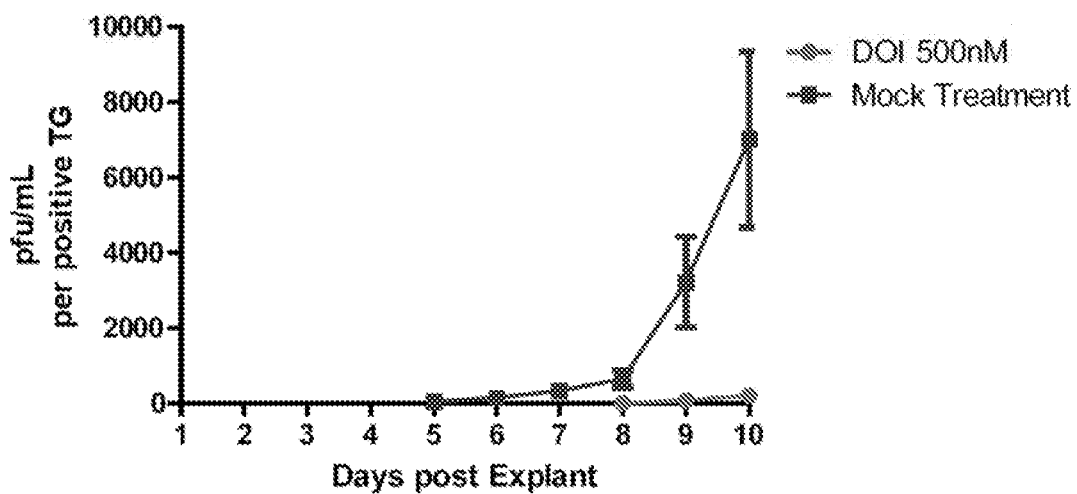

In addition, the 5HT agonist, DOI significantly inhibited the degree of reactivation and amount of infectious virus shed from latent neurons. Analysis of average total reactivated infectious virus (PFU/ml/TG; FIG. 15A) or total reactivated infectious virus per positive TG (PFU/ml/positive TG; FIG. 15B) both indicate that DOI suppressed HSV reactivation, active replication, and shedding of infectious virus from latent neurons relative to mock treated neurons.

TABLE 6

| Days post-Explant | DOI 500 nM | Mock |
|---|---|---|
| 1 | 0/7 (0%) | 0/7 (0%) |
| 2 | 0/7 (0%) | 0/7 (0%) |
| 3 | 0/7 (0%) | 0/7 (0%) |
| 4 | 0/7 (0%) | 0/7 (0%) |
| 5 | 0/7 (0%) | 2/7 (28.6%) |
| 6 | 0/7 (0%) | 4/7 (57.1%) |
| 7 | 0/7 (0%) | 4/7 (57.1%) |
| 8 | 1/7 (14.3%) | 5/7 (71.4%) |
| 9 | 1/7 (14.3%) | 5/7 (71.4%) |
| 10 | 2/7 (28.6%) | 5/7 (71.4%) |

Example 8: Spheroid Tubule Growth Assay

Figure 16:
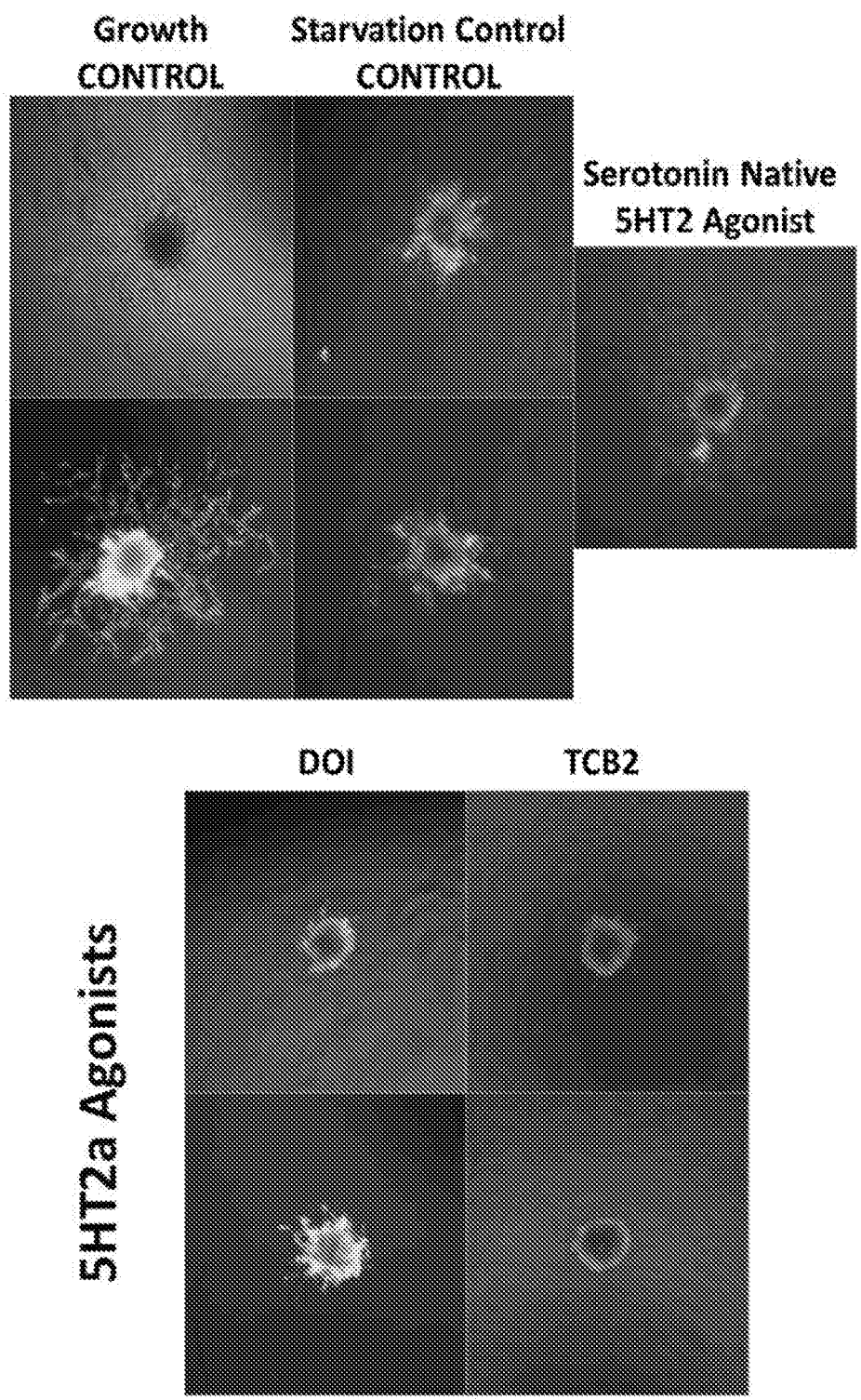
FIG. 16 is a series of fluorescent micrographs showing the effect of $5HT_{2A}$ receptor agonists on vascular tubule growth from tissue-like spheroids.

Serotonin induced vascularization-like replication and tubule growth and in tissue-like spheroids derived from human microvascular endothelial cells (HMEC; FIG. 16). In contrast, multiple 5-HT$_{2A}$ receptor agonists (DOI, TCB2, and 2C2I) unexpectedly abrogated formation of vascular-like tubular growth from HMEC spheroids. HMEC cells were cultured in specially coated U-shaped bottom 96 well plates in order to form tissue-like three-dimension spheroids. Spheroids were subsequently implanted into wells that contained matrigel basement membranes supplemented with vascular endothelial growth factor (VEGF) or starved (Starvation control-no VEGF). Culture media was treated with either serotonin (50 nM), (R-DOI (100 nM), or TCB2 (500 nM) outgrowth from the spheroids of vascular-like structures was monitored microscopically.

Example 9: Specific Killing of Retinoblastoma

Figure 17:
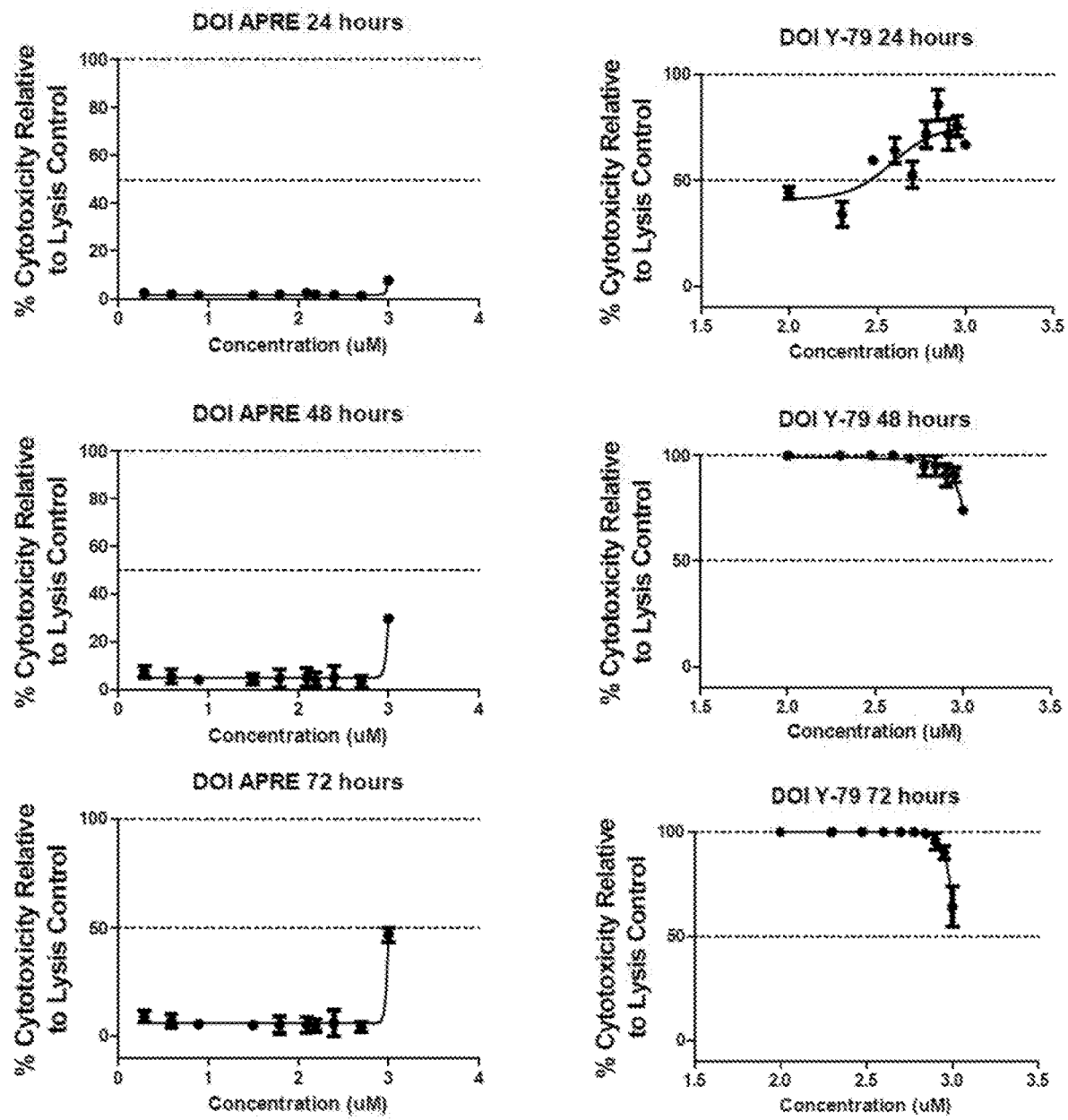
FIG. 17 is a series of graphs showing the effect of R-DOI dose on cytotoxicity of healthy retinal pigment epithelial cells (APRE) and cancerous retinoblastoma cells (Y-79) at 24 hours (top), 48 hours (middle), and 72 hours (bottom).

Healthy (APRE) and cancerous (Y-79) retinal cell lines were treated with varying doses of R-DOI and monitored for cytotoxicity by lysis at 24 hour intervals. Results, shown in FIG. 17, indicate that R-DOI exhibited strong, dose-dependent toxicity of retinoblastoma cells at 24 hours, and the killing effect was saturated at all doses by 48 hours. In comparison, only the highest dose of R-DOI tested exhibited modest cytotoxicity to healthy retinal pigment epithelial cells. Together, these data support the use of 5-HT$_{2A}$ receptor agonists to selectively kill cancerous cells.

OTHER EMBODIMENTS

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of treating viral keratitis in a subject in need thereof, the method comprising administering to the subject a therapeutically effective amount of (R)-2,5-dimethoxy-4-iodoamphetamine (R-DOI) or salt thereof.

2. The method of claim 1, wherein the R-2,5-dimethoxy-4-iodoamphetamine (R-DOI), or a pharmaceutically acceptable salt thereof, is administered ocularly.

3. The method of claim 2, wherein the ocular administration is topical administration, instillation in the conjunctival sac, intravitreal administration, subconjunctival administration, retrobulbar, intracameral, or sub-Tenon's administration.

4. The method of claim 3, wherein the topical administration is by eye drop or gel.

5. The method of claim 1, wherein the R-2,5-dimethoxy-4-iodoamphetamine (R-DOI), or a pharmaceutically acceptable salt thereof, is administered systemically.

* * * * *

SEQUENCE LISTING

```
<160> NUMBER OF SEQ ID NOS: 3

<210> SEQ ID NO 1
<211> LENGTH: 481
<212> TYPE: PRT
<213> ORGANISM: Homo sapiens

<400> SEQUENCE: 1

Met Ala Leu Ser Tyr Arg Val Ser Glu Leu Gln Ser Thr Ile Pro Glu
1               5                   10                  15

His Ile Leu Gln Ser Thr Phe Val His Val Ile Ser Ser Asn Trp Ser
                20                  25                  30

Gly Leu Gln Thr Glu Ser Ile Pro Glu Glu Met Lys Gln Ile Val Glu
            35                  40                  45

Glu Gln Gly Asn Lys Leu His Trp Ala Ala Leu Leu Ile Leu Met Val
        50                  55                  60

Ile Ile Pro Thr Ile Gly Gly Asn Thr Leu Val Ile Leu Ala Val Ser
65                  70                  75                  80

Leu Glu Lys Lys Leu Gln Tyr Ala Thr Asn Tyr Phe Leu Met Ser Leu
                85                  90                  95

Ala Val Ala Asp Leu Leu Val Gly Leu Phe Val Met Pro Ile Ala Leu
                100                 105                 110

Leu Thr Ile Met Phe Glu Ala Met Trp Pro Leu Pro Leu Val Leu Cys
            115                 120                 125

Pro Ala Trp Leu Phe Leu Asp Val Leu Phe Ser Thr Ala Ser Ile Met
        130                 135                 140

His Leu Cys Ala Ile Ser Val Asp Arg Tyr Ile Ala Ile Lys Lys Pro
145                 150                 155                 160

Ile Gln Ala Asn Gln Tyr Asn Ser Arg Ala Thr Ala Phe Ile Lys Ile
                165                 170                 175

Thr Val Val Trp Leu Ile Ser Ile Gly Ile Ala Ile Pro Val Pro Ile
            180                 185                 190

Lys Gly Ile Glu Thr Asp Val Asp Asn Pro Asn Asn Ile Thr Cys Val
        195                 200                 205

Leu Thr Lys Glu Arg Phe Gly Asp Phe Met Leu Phe Gly Ser Leu Ala
    210                 215                 220

Ala Phe Phe Thr Pro Leu Ala Ile Met Ile Val Thr Tyr Phe Leu Thr
225                 230                 235                 240

Ile His Ala Leu Gln Lys Lys Ala Tyr Leu Val Lys Asn Lys Pro Pro
                245                 250                 255

Gln Arg Leu Thr Trp Leu Thr Val Ser Thr Val Phe Gln Arg Asp Glu
            260                 265                 270

Thr Pro Cys Ser Ser Pro Glu Lys Val Ala Met Leu Asp Gly Ser Arg
        275                 280                 285

Lys Asp Lys Ala Leu Pro Asn Ser Gly Asp Glu Thr Leu Met Arg Arg
```

```
                290             295             300
Thr Ser Thr Ile Gly Lys Lys Ser Val Gln Thr Ile Ser Asn Glu Gln
305                     310                 315                 320

Arg Ala Ser Lys Val Leu Gly Ile Val Phe Phe Leu Phe Leu Leu Met
                325                 330                 335

Trp Cys Pro Phe Phe Ile Thr Asn Ile Thr Leu Val Leu Cys Asp Ser
                340                 345                 350

Cys Asn Gln Thr Thr Leu Gln Met Leu Leu Glu Ile Phe Val Trp Ile
                355                 360                 365

Gly Tyr Val Ser Ser Gly Val Asn Pro Leu Val Tyr Thr Leu Phe Asn
                370                 375                 380

Lys Thr Phe Arg Asp Ala Phe Gly Arg Tyr Ile Thr Cys Asn Tyr Arg
385                 390                 395                 400

Ala Thr Lys Ser Val Lys Thr Leu Arg Lys Arg Ser Ser Lys Ile Tyr
                405                 410                 415

Phe Arg Asn Pro Met Ala Glu Asn Ser Lys Phe Phe Lys Lys His Gly
                420                 425                 430

Ile Arg Asn Gly Ile Asn Pro Ala Met Tyr Gln Ser Pro Met Arg Leu
                435                 440                 445

Arg Ser Ser Thr Ile Gln Ser Ser Ile Ile Leu Leu Asp Thr Leu
                450                 455                 460

Leu Leu Thr Glu Asn Glu Gly Asp Lys Thr Glu Glu Gln Val Ser Tyr
465                 470                 475                 480

Val

<210> SEQ ID NO 2
<211> LENGTH: 471
<212> TYPE: PRT
<213> ORGANISM: Homo sapiens

<400> SEQUENCE: 2

Met Asp Ile Leu Cys Glu Glu Asn Thr Ser Leu Ser Ser Thr Thr Asn
1               5                   10                  15

Ser Leu Met Gln Leu Asn Asp Asp Thr Arg Leu Tyr Ser Asn Asp Phe
                20                  25                  30

Asn Ser Gly Glu Ala Asn Thr Ser Asp Ala Phe Asn Trp Thr Val Asp
                35                  40                  45

Ser Glu Asn Arg Thr Asn Leu Ser Cys Glu Gly Cys Leu Ser Pro Ser
                50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
                100                 105                 110

Leu Met Ser Leu Ala Ile Ala Asp Met Leu Leu Gly Phe Leu Val Met
                115                 120                 125

Pro Val Ser Met Leu Thr Ile Leu Tyr Gly Tyr Arg Trp Pro Leu Pro
                130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
```

```
                180                 185                 190
Phe Leu Lys Ile Ile Ala Val Trp Thr Ile Ser Val Gly Ile Ser Met
            195                 200                 205

Pro Ile Pro Val Phe Gly Leu Gln Asp Asp Ser Lys Val Phe Lys Glu
        210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Gly Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
        290                 295                 300

Ser Tyr Thr Gly Arg Arg Thr Met Gln Ser Ile Ser Asn Glu Gln Lys
305                 310                 315                 320

Ala Cys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350

Cys Asn Glu Asp Val Ile Gly Ala Leu Leu Asn Val Phe Val Trp Ile
        355                 360                 365

Gly Tyr Leu Ser Ser Ala Val Asn Pro Leu Val Tyr Thr Leu Phe Asn
        370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Asn Ser
            420                 425                 430

Lys Gln Asp Ala Lys Thr Thr Asp Asn Asp Cys Ser Met Val Ala Leu
        435                 440                 445

Gly Lys Gln His Ser Glu Glu Ala Ser Lys Asp Asn Ser Asp Gly Val
        450                 455                 460

Asn Glu Lys Val Ser Cys Val
465                 470

<210> SEQ ID NO 3
<211> LENGTH: 458
<212> TYPE: PRT
<213> ORGANISM: Homo sapiens

<400> SEQUENCE: 3

Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
                20                  25                  30

Ile Val Thr Asp Ile Phe Asn Thr Ser Asp Gly Gly Arg Phe Lys Phe
            35                  40                  45

Pro Asp Gly Val Gln Asn Trp Pro Ala Leu Ser Ile Val Ile Ile Ile
        50                  55                  60

Ile Met Thr Ile Gly Gly Asn Ile Leu Val Ile Met Ala Val Ser Met
65                  70                  75                  80
```

-continued

```
Glu Lys Lys Leu His Asn Ala Thr Asn Tyr Phe Leu Met Ser Leu Ala
                 85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
290                 295                 300

Asn Glu Arg Lys Ala Ser Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
450                 455
```